US010076293B2

(12) United States Patent
Sehnert et al.

(10) Patent No.: US 10,076,293 B2
(45) Date of Patent: Sep. 18, 2018

(54) RAPID FRAME-RATE WIRELESS IMAGING SYSTEM

(71) Applicant: Carestream Health, Inc., Rochester, NY (US)

(72) Inventors: William J. Sehnert, Fairport, NY (US); Samuel Richard, Rochester, NY (US); John Yorkston, Penfield, NY (US); Xiaohui Wang, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 231 days.

(21) Appl. No.: 14/430,561

(22) PCT Filed: Oct. 1, 2013

(86) PCT No.: PCT/US2013/062823
§ 371 (c)(1),
(2) Date: Mar. 24, 2015

(87) PCT Pub. No.: WO2014/055488
PCT Pub. Date: Apr. 10, 2014

(65) Prior Publication Data
US 2015/0223767 A1 Aug. 13, 2015

Related U.S. Application Data

(60) Provisional application No. 61/708,846, filed on Oct. 2, 2012.

(51) Int. Cl.
*A61B 6/02* (2006.01)
*G21K 4/00* (2006.01)
(Continued)

(52) U.S. Cl.
CPC .............. *A61B 6/4411* (2013.01); *A61B 6/06* (2013.01); *A61B 6/4007* (2013.01);
(Continued)

(58) Field of Classification Search
CPC . C08F 10/00; C08F 4/643; C08F 4/12; C07D 471/04; C07D 487/04; C07F 3/02;
(Continued)

(56) References Cited

U.S. PATENT DOCUMENTS 6,106,152 A 8/2000 Thunberg
6,208,706 B1 3/2001 Campbell et al.
(Continued)

FOREIGN PATENT DOCUMENTS

CN 101623200 A 1/2010
CN 101933813 A 1/2011
(Continued)

OTHER PUBLICATIONS

International Search Report dated May 6, 2014 for International Application No. PCT/US2013/062823, 3 pages.

*Primary Examiner* — Irakli Kiknadze

(57) ABSTRACT

A method for defining the shape of a radiation beam that is directed toward a subject and to a free-standing imaging detector detects the position and orientation of the imaging detector relative to a radiation source, then adjusts an aperture that lies in the path of the radiation beam to shape the beam for incidence on a predetermined area of the detector according to the detected imaging detector position. The radiation source is energized to emit the shaped radiation beam and the image data about the subject is acquired from the imaging detector.

20 Claims, 34 Drawing Sheets

(51) Int. Cl.
*A61B 6/00* (2006.01)
*A61B 6/06* (2006.01)
*G21K 1/04* (2006.01)

(52) U.S. Cl.
CPC .......... *A61B 6/4021* (2013.01); *A61B 6/4233* (2013.01); *A61B 6/4405* (2013.01); *A61B 6/4441* (2013.01); *A61B 6/464* (2013.01); *A61B 6/487* (2013.01); *A61B 6/547* (2013.01); *A61B 6/56* (2013.01); *A61B 6/563* (2013.01); *A61B 6/587* (2013.01); *A61B 6/4283* (2013.01); *A61B 6/467* (2013.01); *A61B 6/481* (2013.01); *A61B 6/542* (2013.01); *A61B 6/588* (2013.01); *G21K 1/046* (2013.01)

(58) Field of Classification Search
CPC ....... A61B 6/06; A61B 6/4007; A61B 6/4021; A61B 6/4233; A61B 6/4283; A61B 6/4405; A61B 6/4411; A61B 6/4441; A61B 6/464; A61B 6/105; A61B 6/447; A61B 6/548; A61B 6/0457; A61B 6/102; A61B 6/467; A61B 6/08; A61B 6/506; A61B 6/145; A61B 6/588; A61B 6/14; A61B 6/4258; A61B 6/4435; A61B 6/502; A61B 6/508; A61B 5/0035; A61B 5/0088; A61B 6/032; A61B 6/4035; A61B 6/44; A61B 6/025; A61B 6/035; A61B 6/04; A61B 6/0492; A61B 6/4085; A61B 6/4429; A61B 6/4447; A61B 6/4452; A61B 6/4482; A61B 6/461; A61B 6/50; A61B 6/527; G01D 5/2417; G05B 19/19; G05B 2219/43162; G06F 3/044; H03K 17/962; H03K 17/975; H03K 2017/9602; H03K 2217/96062; A61N 5/1017; A61N 5/1049; A61N 2005/1091; A61N 2005/105; A61N 2005/1059; A61N 5/10; A61N 5/1045; A61N 5/1065; A61N 2005/1019; A61N 2005/1022; A61N 2005/1051; A61N 2005/1097; A61N 5/1001; A61N 5/1048; A61N 5/1064
USPC .............. 378/4, 15, 20, 57, 62, 65, 147–153
See application file for complete search history.

(56) References Cited

U.S. PATENT DOCUMENTS

| | | | | |
|---|---|---|---|---|
| 7,120,231 | B2 * | 10/2006 | Spahn | A61B 6/06 250/515.1 |
| 7,906,770 | B2 * | 3/2011 | Otto | A61N 5/1031 250/492.3 |
| 8,767,909 | B2 * | 7/2014 | Vogtmeier | A61B 6/025 378/193 |
| 8,971,493 | B2 * | 3/2015 | Zhang | A61B 5/7285 378/150 |
| 2004/0057552 | A1 * | 3/2004 | Collins | A61N 5/1084 378/65 |
| 2004/0066907 | A1 * | 4/2004 | Fadler | A61B 6/0457 378/197 |
| 2005/0054915 | A1 | 3/2005 | Sukovic et al. | |
| 2011/0013220 | A1 | 1/2011 | Sabol et al. | |
| 2011/0051895 | A1 | 3/2011 | Vogtmeier et al. | |
| 2011/0080992 | A1 * | 4/2011 | Dafni | A61B 6/032 378/9 |
| 2011/0158385 | A1 | 6/2011 | Nakatsugawa et al. | |
| 2012/0230473 | A1 | 9/2012 | Stagnitto et al. | |

FOREIGN PATENT DOCUMENTS

| | | | | |
|---|---|---|---|---|
| CN | 102018522 A | | 4/2011 | |
| CN | 102088909 | | 6/2011 | |
| DE | 103 20 862 A1 | | 12/2004 | |
| DE | 102010041201 | | 3/2012 | |
| EP | 0 998 173 A1 | | 5/2000 | |
| FR | 2 967 343 A1 | | 5/2012 | |
| JP | 2001-029339 | | 2/2001 | |
| JP | 2002-119500 | | 4/2002 | |
| JP | 2005-000470 | | 1/2005 | |
| JP | 2008-036314 | | 2/2008 | |
| JP | 2009-507548 | | 2/2009 | |
| JP | 2011-520233 | | 7/2011 | |
| WO | 2002-119500 | | 4/2002 | |
| WO | 2005/013828 | | 2/2005 | |
| WO | WO 2005013828 A1 * | | 2/2005 | A61B 6/032 |
| WO | 2009/136349 | | 11/2009 | |
| WO | WO 2010070560 A2 * | | 6/2010 | A61B 6/025 |
| WO | 2013/008685 | | 1/2013 | |
| WO | 2014/055488 | | 4/2014 | |

\* cited by examiner

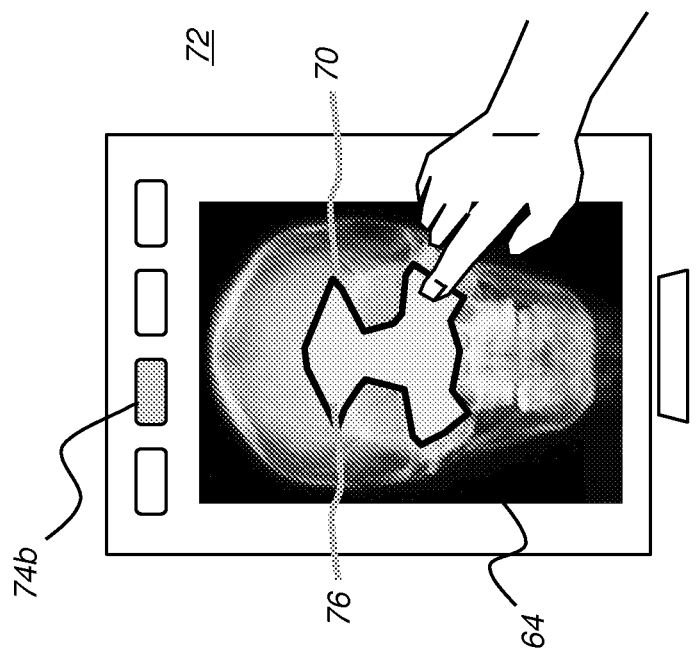
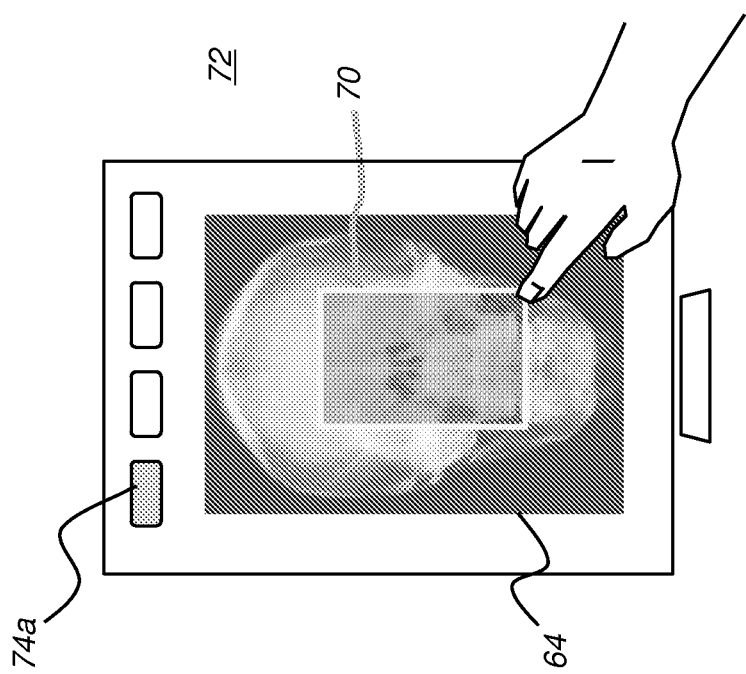
FIG. 6A
FIG. 6B

Application of C-arms

- Mini C-arms
  - Pacemaker / line placement
  - Orthopedics
- Mobile C- arms
  - General Surgery
  - Minimally invasive surgery
  - Cardiology / Electrophysiology
  - Pain Management
  - Endoscopy
- Stationary C-arms
  - Interventional Radiology
  - Interventional Cardiology
  - Interventional Neurology

*FIG. 15*

Detector components

Certain exemplary fast frame-rate wireless cassette-sized x-ray image detector powered by an internal battery embodiments can provide capabilities sufficient for exemplary imaging system capabilities set forth herein. For example, a fast frame rate DR detector can comprise the following in whole or in part and/or in combination:

| | |
|---|---|
| Active area: | minimum 4x4 inch, 6x6 inch, to a max of 17x17 inch |
| Pixel pitch: | minimum of ~50um, maximum of ~500um |
| Packaging dimensions: | a maximum of 1 inch larger than the active area and a maximum thickness of the package of 1 inch |
| Weight: | maximum weight of ~20lbs |
| Substrate: | rigid glass or flexible material (e.g., metal, plastic, glass) |
| Readout Speed: | minimum of ~2 fps up to a maximum of ~60 fps to 120 fps. |
| Readout Speed (ROI): | minimum of ~2 fps up to a maximum of ~60 fps to 120 fps. |
| Data transfer: | preferred embodiment is wireless with high enough bandwidth to allow real time imaging. Tethered detector would also work. (example: 6" detector with 75um pixels, 1byte/pixel, 60 fps. = ~250 MBytes/sec) |
| Detector storage: | one exemplary embodiment is for the detector to have sufficient on board memory to allow storage of ~30 seconds of data that is then transferred at a later time at a slower bandwidth to the external computer/display system. (one exemplary embodiment is to use data compression inside the detector to reduce the amount of data that needs to be transferred). |
| Power supply: | exemplary embodiment for non-tethered option is rechargeable, replaceable battery pack. (as in conventional wireless DR detectors) |
| Detector temperature sensor: | temperature sensor that can communicate to turn off X-ray source when the detector gets too warm, or over threshold |
| Detector/Radiation source predictor | to inform user (e.g., dynamic indicator green/yellow/red, time or number of images) for detector and/or also x-ray source operating status |
| Calibration/correction: | -including temperature based offset correction for the detector |

*FIG. 16*

RAPID FRAME-RATE WIRELESS IMAGING SYSTEM

CROSS REFERENCE TO RELATED APPLICATIONS

This application is a 371 national stage application of earlier filed international application Serial No. PCT/US2013/062823, filed on Oct. 1, 2013 entitled "RAPID FRAME-RATE WIRELESS IMAGING SYSTEM", in the names of Sehnert et al., which itself claims the benefit of earlier filed Provisional Application Ser. No. 61/708,846, filed on Oct. 2, 2012, entitled "RAPID FRAME-RATE WIRELESS IMAGING SYSTEM", in the names of Sehnert et al., all of which are incorporated herein by reference in their entirety.

FIELD OF THE INVENTION

The invention relates generally to the field of medical imaging; more particularly to a method for control of components of a portable x-ray fluoroscopic imaging apparatus with a detachable x-ray detector.

BACKGROUND OF THE INVENTION

Fluoroscopy provides near real-time visualization of internal anatomy of a patient, with the ability to monitor dynamic processes, including tracking the relative motion of various types of features such as probes or other devices, fluids, and structures. Fluoroscopy is used, for example to help in diagnosis and to position the patient for subsequent image recording or to position and manipulate various types of devices for interventional procedures.

The block diagram of FIG. 1 shows components in the imaging path of a conventional fluoroscopy system 10 for obtaining images of a patient 14 or other subject. Radiation from an x-ray source 20 that typically uses a collimator 22 and filtration 24 is directed through a patient 14 to an image intensifier 30. Generally a grid 32 is provided. A camera 40 then captures successive video frames from the x-ray exposure and generates images that are displayed on a display monitor 44.

To reduce the exposure of the patient to ionizing radiation, conventional fluoroscopy practices use the collimator 22 to limit the size of the exposure field as much as possible. Adjustments to collimator 22 are made using an initial "scout image" to ascertain how well the radiation beam is centered and how much adjustment of the collimators can be allowed in order to direct radiation to the region of interest (ROI) for a particular patient 14. The practitioner views the scout image and makes adjustments accordingly, then begins the active imaging sequence for fluoroscopy. This procedure is time-consuming and approximate, sometimes requiring repetition of the adjustment to correct for error. Moreover, movement of the patient or ongoing progress of a contrast agent or probe or other device can cause the ROI to shift, requiring that the imaging session be repeatedly paused in order to allow for collimator readjustment.

As digital radiography (DR) imaging receivers steadily improve in image quality and acquisition speed, it is anticipated that these devices can be increasingly employed not only for conventional radiography imaging, but also for fluoroscopy applications, effectively eliminating the need for the dedicated image intensifier hardware used with conventional fluoroscopy systems such as that shown in FIG. 1.

SUMMARY OF THE INVENTION

An aspect of this application is to advance the art of medical rapid frame-rate wireless imaging (e.g., fluoroscopy).

Another aspect of this application to address in whole or in part, at least the foregoing and other deficiencies in the related art.

It is another aspect of this application to provide in whole or in part, at least the advantages described herein.

Another aspect of the application is to provide methods and/or apparatus by which medical rapid frame-rate wireless imaging can be provided.

Another aspect of this application is to address the need for improvements in providing rapid-frame rate imaging from a portable system.

According to an aspect of the present invention, there is provided a portable radiographic imaging apparatus comprising:
  a wheeled transport frame; and
  a support arm mounted on the frame and having a fixed end that is coupled to a radiation source and, opposite the fixed end, a retractable end, wherein the retractable end seats an imaging detector when the retractable end is extended outward from the frame and retracts into the support arm in a retracted position;
  wherein the imaging detector is removable from the retractable end for free-standing operation with the support arm in the retracted position.

According to an alternate aspect, there is provided a method for defining the shape of a radiation beam that is directed toward a subject and to a free-standing imaging detector, the method comprising:
  a) detecting the position and orientation of the imaging detector relative to a radiation source;
  b) adjusting an aperture that lies in the path of the radiation beam to shape the beam for incidence on a predetermined area of the detector according to the detected imaging detector position;
  c) energizing the radiation source to emit the shaped radiation beam; and
  d) acquiring image data about the subject from the imaging detector.

According to an alternate aspect, there is provided a portable radiographic imaging apparatus comprising:
  a support arm mounted on a frame and having a fixed end that is coupled to a radiation source array that has two or more radiation sources that are individually energizable to emit a radiation beam toward a detector;
  a switching actuator that is energizable to align the radiation beams from each of the two or more radiation sources along the same optical path;
  at least one radiation source temperature sensor element that provides a signal that is indicative of temperature near the energized radiation source; and
  a processor that monitors the signal from the at least one radiation source sensor element and controls at least energization of the two or more radiation sources according to the monitored signal.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 6A is a view of an operator interface for defining the region of interest for a fluoroscopy imaging sequence using a rectangle.

FIG. 6B is a view of an operator interface for defining the region of interest for a fluoroscopy imaging sequence using a mask.

FIG. 15 is a diagram showing exemplary applications of fluoroscopic imaging apparatus.

FIG. 16 is a diagram showing exemplary capabilities of a digital portable flat panel-type radiographic detector (e.g., for use with fluoroscopic imaging apparatus) according to certain exemplary embodiments of the application.

DESCRIPTION OF EXEMPLARY EMBODIMENTS

Figure 1:
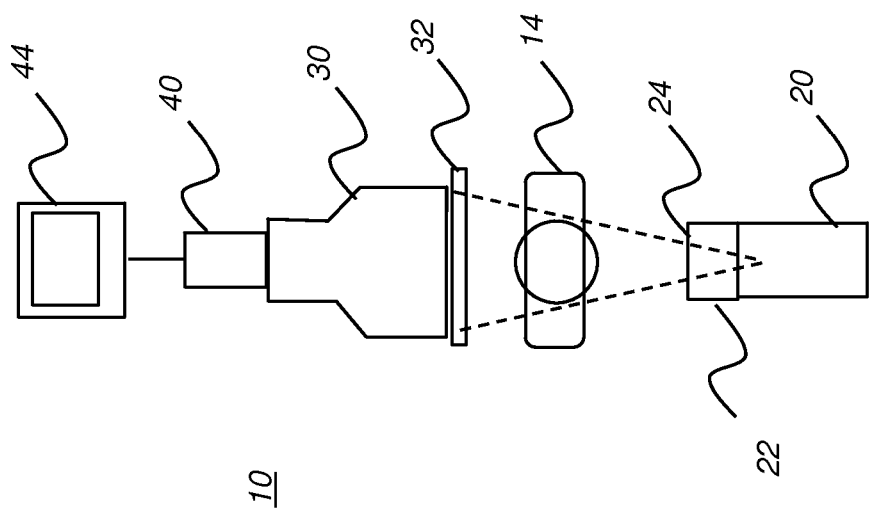
FIG. 1 is a schematic block diagram showing components of a conventional fluoroscopic imaging apparatus.

The following is a detailed description of the preferred embodiments of the invention, reference being made to the drawings in which the same reference numerals identify the same elements of structure in each of the several figures.

Where they are used, the terms "first", "second", and so on, do not necessarily denote any ordinal, sequential, or priority relation, but are simply used to more clearly distinguish one element or set of elements from another, unless specified otherwise. The term "pixel" has its standard meaning, referring to a picture element, expressed as a unit of image data.

In the context of the present disclosure, the terms "viewer", "operator", and "user" are considered to be equivalent and refer to the viewing practitioner or other person who views and manipulates an x-ray image, such as a fluoroscopic image, on a display monitor. A "viewer instruction" can be obtained from explicit commands entered by the viewer on the surface of the display or may be implicitly obtained or derived based on some other user action, such as setting up or initiating an exposure or making a collimator adjustment, for example.

In the context of the present invention, the terms "near video rate" and "near real-time" relate to the response time for image data display. For fluoroscopy, because of detector response limitations and because it is beneficial to help reduce radiation levels, what is considered real-time or near-real-time video presentation is generally at a slower frame refresh rate than rates used for conventional video imaging. Thus, in the context of fluoroscopy imaging for example, a useful "near real-time" refresh rate is at least about 1 or more frames per second.

The term "highlighting" for a displayed feature has its conventional meaning as is understood to those skilled in the information and image display arts. In general, highlighting uses some form of localized display enhancement to attract the attention of the viewer. Highlighting a portion of an image, such as an individual organ, bone, or structure, or a path from one chamber to the next, for example, can be achieved in any of a number of ways, including, but not limited to, annotating, displaying a nearby or overlaying symbol, outlining or tracing, display in a different color or at a markedly different intensity or gray scale value than other image or information content, blinking or animation of a portion of a display, or display at higher resolution, sharpness, or contrast.

Figure 2B:
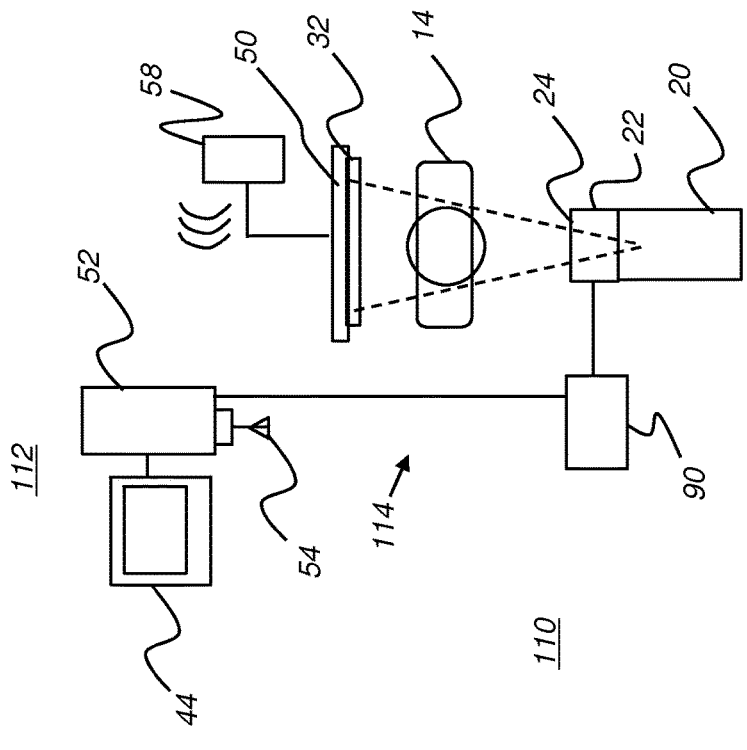
FIG. 2B is a schematic block diagram showing components of a fluoroscopic imaging apparatus using wireless image data transmission.
Figure 2A:
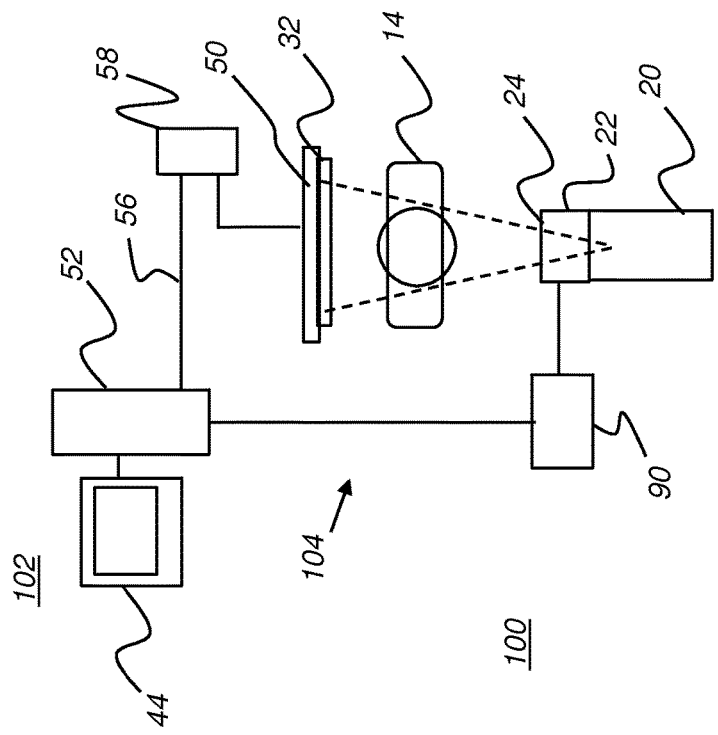
FIG. 2A is a schematic block diagram showing components of a fluoroscopic imaging apparatus using wired image data transmission.

Exemplary embodiments of the application can enable the use of a digital radiography (DR) receiver as the digital image receiver for receiving radiation in the fluoroscopy system and for generating, processing, and transmitting the received image data, as image pixels (picture elements), to a display apparatus for fluoroscopic display. FIGS. 2A and 2B respectively show two general arrangements of system components for a fluoroscopy system 100 that uses an interconnect cable 56 for image data transmission and a fluoroscopy system 110 that employs wireless transmission of image data.

FIG. 2A illustrates fluoroscopy system 100 having a fluoroscopy capture apparatus 104 that includes DR receiver 50 and an image processing unit 58 that obtains and processes the image data from detector 50 and transmits the processed image data to a host processor 52 through an interconnect cable 56 for providing the image data to a fluoroscopy display apparatus 102 that includes a display monitor 44. Host processor 52 is a computer or workstation or other logic and control processor that obtains the processed fluoroscopy image data and displays the obtained images at near-video rates to the practitioner or other viewer. An imaging controller 90 generates signals that control various aspects of operation of fluoroscopy capture apparatus 104, including the dimensions and placement of the collimator 22 opening, as described in more detail subsequently.

FIG. 2B shows fluoroscopy system 110 that has a fluoroscopy capture apparatus 114 in which image processing unit 58 provides the processed image data of a subject to a fluoroscopy display apparatus 112 in wireless form. Host processor 52 has a wireless receiver element 54 for providing the image data to fluoroscopy display apparatus 112 for viewing on display monitor 44.

For both FIG. 2A and FIG. 2B embodiments, image processing unit 58 may be integrated into DR receiver 50 or may be a separate processor apparatus. Image processing unit 58 may be a dedicated microprocessor, host processor, or other type of computer device, including a device that performs logic instructions that have been encoded in hardware.

An aspect in obtaining processed image data of the subject at near video rates relates to the need for both high-speed data access between DR receiver 50 and image processing unit 58 and high data transmission rates from image processing unit 58 to host processor 52 (FIGS. 2A, 2B). It is noted that this aspect is more pronounced with the wireless transmission of fluoroscopy system 110 in FIG. 2B, since wireless rates are generally slower than data rates with a hard-wired connection and since wireless transmission can be further hindered by intermittent noise and interference. Thus, methods for compacting the image data as much as possible offer one way to help alleviate the potential data transmission bottleneck that can occur with either wired or wireless transmission.

Figure 3:
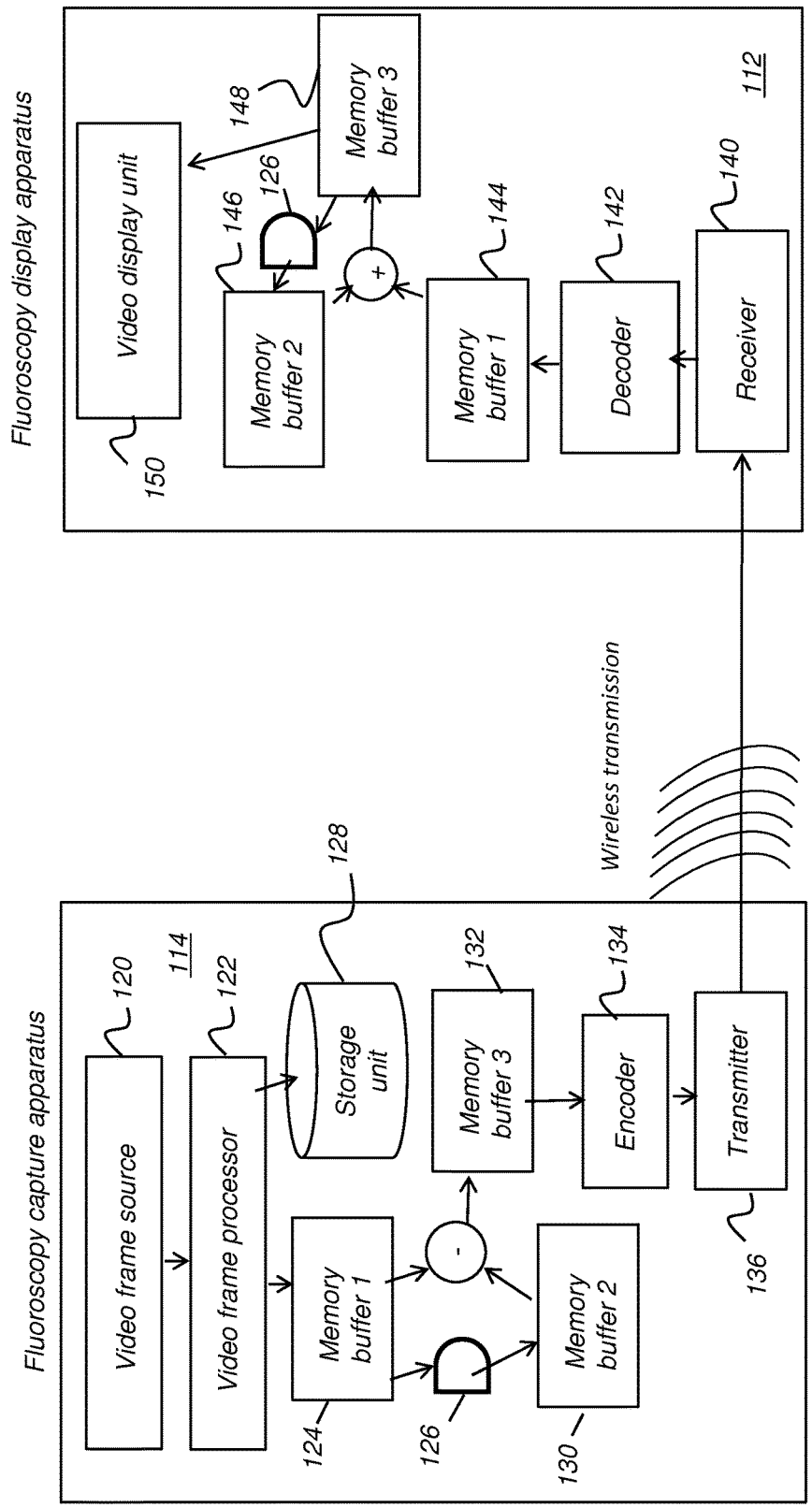
FIG. 3 is a schematic block diagram that shows functional components of a fluoroscopy capture and display apparatus according to embodiments of the present invention.

One method for reducing the bulk amount of data that must be transferred determines the differences between two successive frames and provides only the data that is indicative of the difference. The block diagram of FIG. 3 gives a functional overview of components for wireless transmission in the embodiment of fluoroscopy system 110 shown in FIG. 2B that uses difference information between successive image frames. At fluoroscopy capture apparatus 114, a video frame source 120 includes the DR receiver 50 components that obtain the digital data that is representative of the received radiation transmitted through patient 14 or other subject. A video frame processor 122, provided in image processing unit 58 in the FIGS. 2A and 2B embodiments, processes the received frame of image data for rendering quality and outputs the processed frame into a memory buffer 124. Utilities that can be used for improving rendering quality include, for example, tone scale adjustment, unsharp masking, and other functions. Optionally, the image data is also sent to a storage unit 128 for longer term archival. A first memory buffer 124 contains the current image frame. A second memory buffer 130 contains image content for the preceding frame. Processing compares memory buffers 124 and 130 to generate difference data between successive image frames and store this in a third memory buffer 132. The image data contents of third memory buffer 132 are then provided to an encoder 134 for compression and to a transmitter 136 for data transmission. This provides compressed fluoroscopy data for transmission to fluoroscopy display apparatus 112. For processing the next frame of image data, after a delay 126, data from memory buffer 124 becomes memory buffer 130 data.

Continuing with the sequence shown in FIG. 3, the transmitted data goes to fluoroscopy display apparatus 112. A receiver 140 receives the compressed image data and provides this data to a decoder 142. The decoded data then goes to a memory buffer 144 as a difference image. This image data is combined with image data for the previous frame that is in a memory buffer 146 to form image data that is then stored in a memory buffer 148. Image data from memory buffer 148 is then provided to a video display unit 150 for display on the display monitor and to memory buffer 146 for processing the next frame. Delay 126 is provided between transfer of data from memory buffer 148 to memory buffer 146.

With respect to the sequence described with reference to FIG. 3, it should be noted that the first image frame is handled differently, stored in the appropriate memory buffer to provide initial reference data for subsequent processing. Although described primarily with reference to the wireless embodiment of FIG. 2B, the same basic processing sequence used within capture apparatus 114 and display apparatus 112 in FIG. 3 can also be used in the hard-wired embodiment of FIG. 2A.

The difference scheme used in the sequence described with reference to FIG. 3 can help to reduce the amount of image data that is transferred in wired or wireless form. Difference data can be transmitted for either or both the region of interest or the background region. However, there can still be a considerable amount of data to be transferred. Moreover, not all of the transferred data may be as important/relevant for the clinical or diagnostic function. There may be some image data for which compression is not desirable, where compression results in any loss of image content. Some types of image compression are lossy, so that some amount of image data can be compromised when compression is used. The resulting loss of data may make compression undesirable for some portion of the image content.

Image data compression techniques can also be lossless or lossy and embodiments of the application can employ both types of compression for different types of image content to reduce data transferred.

Figure 4B:
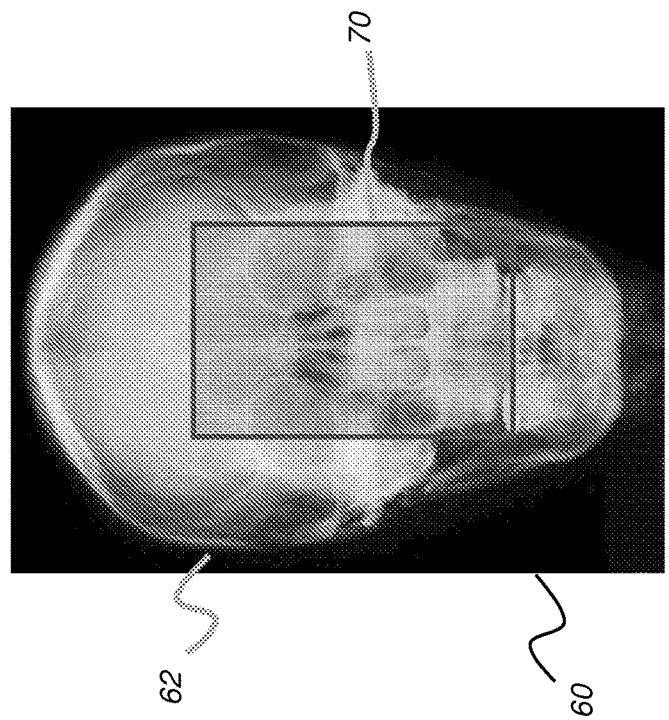
FIG. 4B is a view of the image of FIG. 4A showing a rectangular region of interest, defined according to an embodiment of the present invention.
Figure 4A:
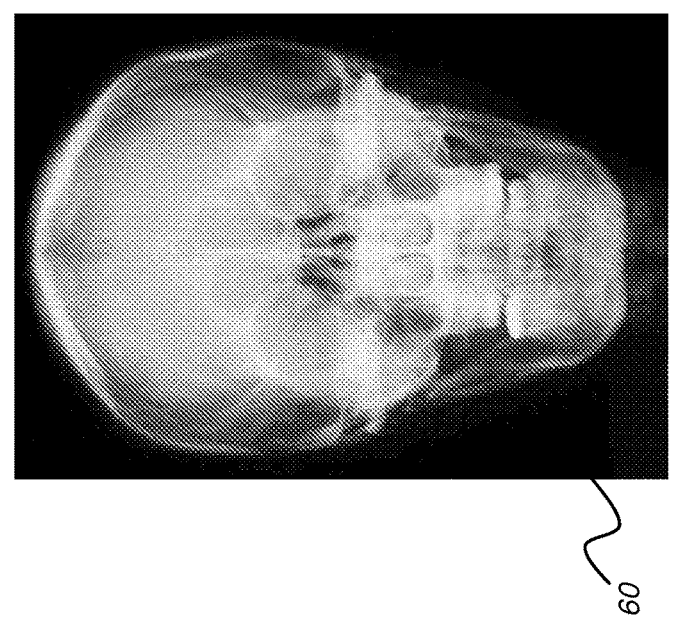
FIG. 4A is a plan view that shows a fluoroscopy image of a patient's head.

FIG. 4A shows a fluoroscopy image 60 that includes a patient's head. For a particular procedure, only a portion of the patient's head is of interest. As shown in FIG. 4B, there is a region of interest (ROI) 70, identified as a rectangular area in this example. The balance of image 60, exclusive of region of interest 70, is a background region 62.

Figure 5:
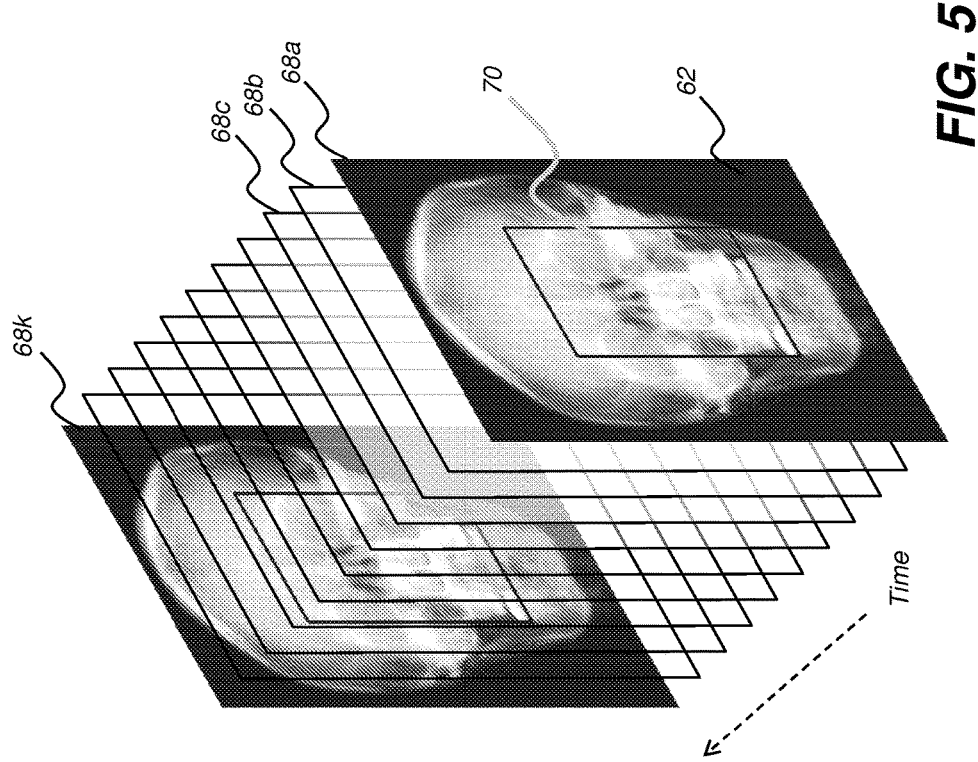
FIG. 5 is a diagram that shows successive image frames in a fluoroscopy imaging sequence.

FIG. 5 shows a series of successive image frames 68a, 68b, 68c . . . 68k in a small portion of an example fluoroscopy sequence. As can be seen, the same anatomy is imaged in each image frame. Of primary interest to the practitioner is region of interest 70 within each frame; background region 62 is of less value for the procedure that is being performed. For this reason, embodiments of the present method allow different types of image processing and image data compression and transmission for the two (or more) portions of the image, e.g., for region of interest 70 and background region 62. This allows the display of region of interest 70 at higher resolution and contrast than the display of background region 62, for example.

Regardless of the method that is employed for image compression and transmission, region of interest 70 is identified, relative to the image area of the digital detector or receiver, DR receiver 50 (FIGS. 2A, 2B). This can be done in a number of ways, such as those shown in the examples of FIGS. 6A through 6D.

Some type of viewer instruction or action is used to define the region of interest. FIGS. 6A and 6B show identifying region of interest 70 according to a viewer instruction entered/indicated on the operator interface, termed a Graphical User Interface (GUI) 72 on display monitor 44 (FIGS. 2A, 2B). In the example shown in FIG. 6A, a touch screen interface allows the viewer to outline region of interest 70 directly on a displayed basis image 64. Basis image 64 is a single fluoroscopy image that is optionally obtained as a part of initial setup for the fluoroscopy session. An optional control button 74a allows for entry of an operator instruction that enables outlining onto the displayed basis image.

FIG. 6B shows definition of region of interest 70 using a mask 76 that is identified or defined by the user with reference to the basis image. An operator instruction at a control button 74b specifies this function.

User tracing or placement of a shape that defines a region of interest relative to a basis image can be performed in a number of ways, using standard user interface tools and utilities, that include a touch screen or use of a computer mouse or stylus or other pointer.

Figure 6D:
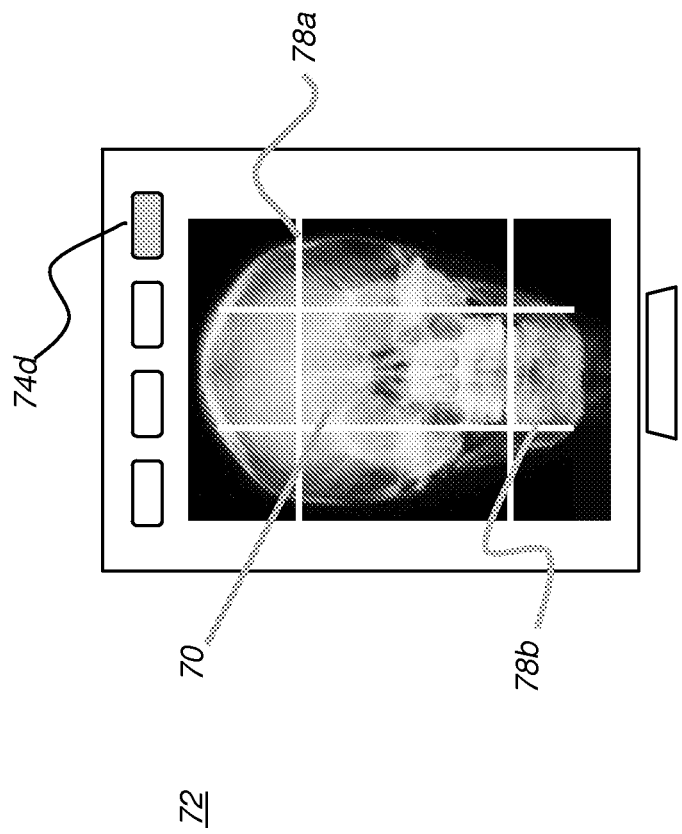
FIG. 6D is a view of an operator interface for defining the region of interest for a fluoroscopy imaging sequence using a collimator setting.
Figure 6C:
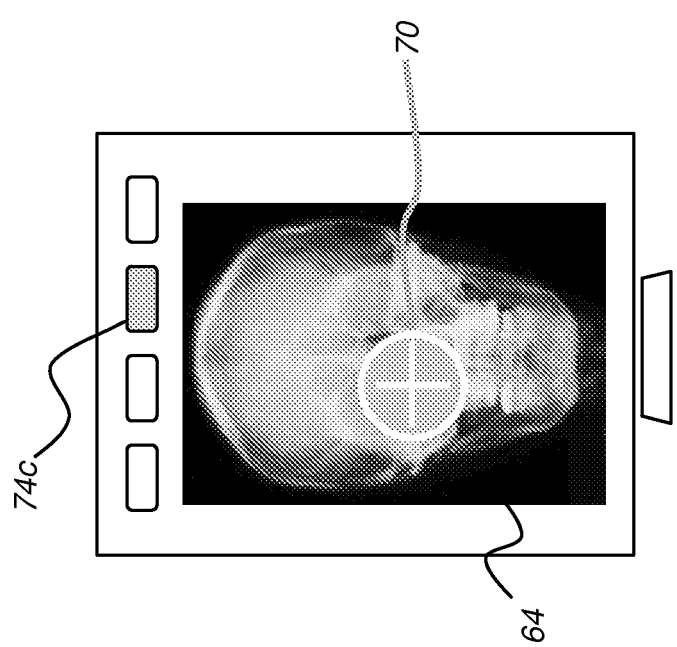
FIG. 6C is a view of an operator interface for defining the region of interest for a fluoroscopy imaging sequence using a device or object.

The example of FIG. 6C shows a default arrangement that can be used. A viewer instruction entered on a control button 74c instructs the system to track a device or object, such as an instrument, camera, probe, needle, tube, or other object that is placed on or inserted into the patient anatomy being imaged. Region of interest 70 is defined in the vicinity of the tracked device or object and can have an operator entered or a default size, such as a given diameter about the object or device.

The example illustrated in FIG. 6D shows another alternate embodiment in which the operator instruction, entered using a control button 74d, allows the system to define the boundaries of region of interest 70 according to the settings of collimator 22 blades (FIGS. 2A, 2B), as adjusted by the viewer. In the example of FIG. 6D, lines 78a and 78b show the collimator blade settings, effectively providing a rectangular area as region of interest 70. On some systems, collimator blades are motor controlled, allowing the viewer to adjust and view settings for the area of interest as part of the overall equipment setup.

According to an alternate embodiment of the present method/apparatus, the operator can adjust collimator blade positions and observe blade repositioning directly on the display screen, allowing the system to adopt and change ROI boundaries according to blade settings. To obtain suitable coordinates for ROI identification, the imaging system detects the positions of collimator blades, and translates this positional information into corresponding coordinates on the detector for ROI identification.

Thus, in various ways, an ROI is identified, wherein the ROI maps to, or relates to, the image area of the digital detector of the imaging system. The viewer instruction that identifies/defines the ROI may be explicitly entered using the basis image as previously described, or may be inferred from a collimator or other adjustment. Alternately, the viewer instruction may simply be a command or instruction to prepare for obtaining images, thus prompting the imaging system to use a default ROI definition based on the type of image being obtained or based on sensed settings of the collimator, for example.

Once region of interest 70 is defined on the basis image, the viewer can enter an explicit instruction that indicates completion of this process. Alternately, the given settings are used automatically and exposure can begin. The specified region of interest settings are maintained until specifically adjusted by the viewer.

Figure 7:
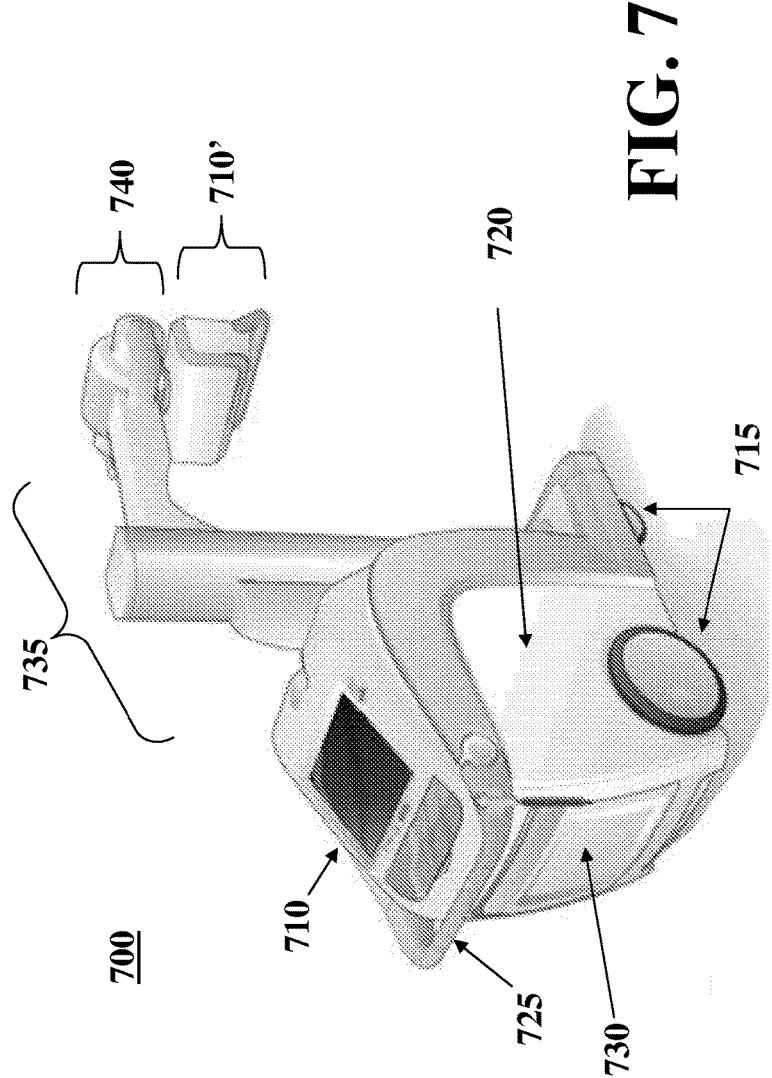
FIG. 7 is a diagram that shows a perspective view of a mobile radiography unit capable of fluoroscopy according to an embodiment of the application.

FIG. 7 is a diagram that shows a perspective view of a mobile radiography unit capable of fluoroscopy according to an embodiment of the application. The exemplary mobile x-ray or radiographic apparatus of FIG. 7 can be employed for computed radiography (CR) and/or digital radiography (DR). As shown in FIG. 7, a mobile radiography apparatus 700 can include a moveable transport frame 720 that includes a first display 710 and an optional second display 710' for display relevant information such as obtained images and related data. As shown in FIG. 7, the second display 710' can be pivotable mounted at the x-ray source 740 to be viewable/touchable from a 360 degree area around the tube head.

The displays 710, 710' can implement or control (e.g., touch screens) functions such as generating, storing, transmitting, modifying, and printing of an obtained image(s) and can include an integral or separate control panel (not shown) to assist in implementing functions such as generating, storing, transmitting, modifying, and printing of an obtained image(s).

For mobility, the mobile radiographic apparatus 700 has one or more wheels 715 and one or more handle grips 725, typically provided at waist-, arm-, or hand-level, that help to guide the mobile radiography apparatus 700 to its intended location. A self-contained battery pack (e.g., rechargeable) typically provides source power, which can reduce or eliminate the need for operation near a power outlet. Further, the self-contained battery pack can provide for motorized transport.

For storage, the mobile radiography apparatus 700 can include an area/holder for holding/storing one or more digital detectors or computed radiography cassettes. The area/holder can be storage area 730 (e.g., disposed on the frame 720) configured to removably retain at least one digital radiography (DR) detector. The storage area 730 can be configured to hold one or more detectors and can also be configured to hold one size or multiple sizes of detectors.

Mounted to frame 720 is a support column 735 that supports an x-ray source 740, also called an x-ray tube, tube head, or generator that can be mounted to the support column 735. In the embodiment shown in FIG. 7, the support column 735 can include a second section that extends outward a fixed/variable distance from a first section where the second section is configured to ride vertically up and down the first section to the desired height for obtaining the image. In another embodiment, the tube head or x-ray source 740 can be rotatably coupled to the support column 735. In another exemplary embodiment, an articulated member of the support column 735 that bends at a joint mechanism can allow movement of the x-ray source 740 over a range of vertical and horizontal positions. Height settings for the x-ray source 740 can range from low height for imaging feet and lower extremities to shoulder height and above for imaging the upper body portions of patients in various positions.

Figure 8:
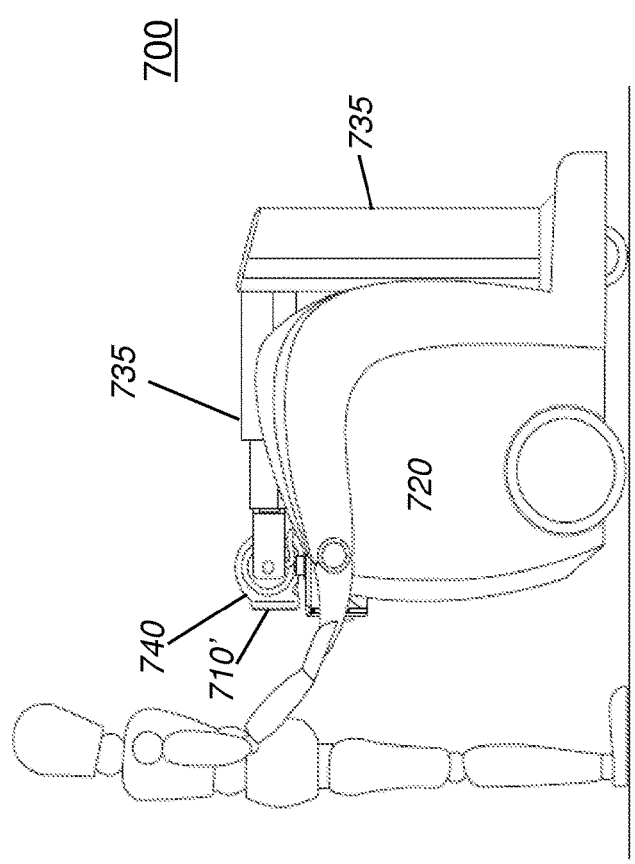
FIG. 8 is a diagram that shows a perspective view of a mobile radiography unit of FIG. 7 in a transport position.

As shown in FIG. 8, for ease during transport of the mobile radiography apparatus 700, the support member 735 and x-ray source 740 can be arranged close to frame 720. As shown in FIG. 8, the second display 710' can be moved to a viewable position (e.g., operable) during transport of the mobile radiography apparatus 700. In one embodiment, the first display 710 can be disabled during transport. When the mobile radiography apparatus 700 is to be used, the support member 735 and x-ray source 740 can be extended from the frame 720 for proper positioning (e.g., by the operator, a user, or x-ray technician) and the second display 710' moved to viewable position as shown in FIG. 7.

According to exemplary embodiments of the application, the first display 710 and the second display 710' can provide information such as but not limited to: (i) general information such as date, time, environment conditions, and the like; (ii) unit information such as model serial number, operating instructions, warning information, and the like; (iii) patient data, such as patient name, room number, age, blood type, and the like; (iv) indicators such as but not limited to cart power/battery indicators, detector status (e.g., on/off), wireless signal strength/connectivity, grid alignment aides, cart diagnostics and/or (v) imaging/procedure information, such as the exam type, exposure information, and the like.

According to embodiments of the application, the first display 710 and the second display 710' can provide capabilities/functionality to the mobile radiography apparatus 700 such as but not limited to: (i) view and/or change x-ray exposure parameters, tube/generator/technique settings; (ii) view and/or change image information, such as a list of views (e.g., body part & projection) to perform for the patient, relevant information about those views, the ability to select a view to perform, and an x-ray image of an acquired view; (iii) display and/or change patient information, such as: Patient Name, Room number, Patient ID, date of birth (e.g., to confirm that the correct patient); (iv) display and/or change a Patient Worklist, such as a list of exams to perform and allow the user to select an exam (In one embodiment, such a patient worklist can be automatically updated (e.g., synchronized to a master/hospital/doctor worklist) using a wired or wireless network/connection. In one embodiment, the mobile radiography apparatus 700 can highlight/indicate new exams (e.g., on the second display 710') upon receipt of the scheduled examination); (v) display generator/source current values and controls to change those values, such as: kVp, mA, mAs, Time, ECF, focal spot, collimator, filter, AEC, grid; (vi) display detector selection and allow the technician to select/activate a different detector; (vii) display recently acquired images and allow editing of those images, exemplary acquired (e.g., recently) or previous images can be displayed full size, partial size or with corresponding image information; (viii) display previously acquired images (e.g., related prior images of a patient) and allow editing of those images; or (ix) display a video of what is in front of the mobile radiography apparatus 700 during transport, e.g., using a video camera located on the other side (e.g., front side of a mobile x-ray imaging apparatus 700).

In the context of the present disclosure, an original or primary image of a subject that is acquired by a system of the present application can include raw image data or may be image data that is automatically pre-processed by the x-ray system itself (so that the raw data is not directly available to users of the system). This can be termed the "primary", "original", or "acquired" image of the subject and can include image data from scanned film, from a computed radiography (CR) imaging system, or from a digital radiography (DR) system, for example.

In the context of the present disclosure, a "prior image" is an image for a patient that was acquired during a previous visit, and preferably, the prior image can be relevant (e.g., same body part) to a current examination to be performed, which will result in a primary image. The capability to view prior images before a current examination to be performed (e.g., for the same patient) including information about imaging techniques used in the prior images can help the technician to obtain a high quality image for the current examination. In one embodiment, a "copy technique" operator action can import specific exposure settings from a selected (e.g., desirable, ideal) prior image among a plurality of prior images for the technician. Prior images can also be related to an identifiable condition or an area of interest in the object to be imaged. Embodiments of systems and/or methods for management and display of prior images can provide a controllable association between prior images and can provide tools for management of that association.

Conventional solutions for image storage and retrieval and for association of multiple images obtained for the same patient employ the PACS (Picture Archiving and Communication System) and various conventional database tools. Thus, as described herein, the PACS is an image store accessible to a radiographic imaging system or an agent thereof to retrieve images therefrom. In one embodiment, the PACS can implement the Digital Imaging and Communications in Medicine (DICOM) data interchange standard.

Figure 9:
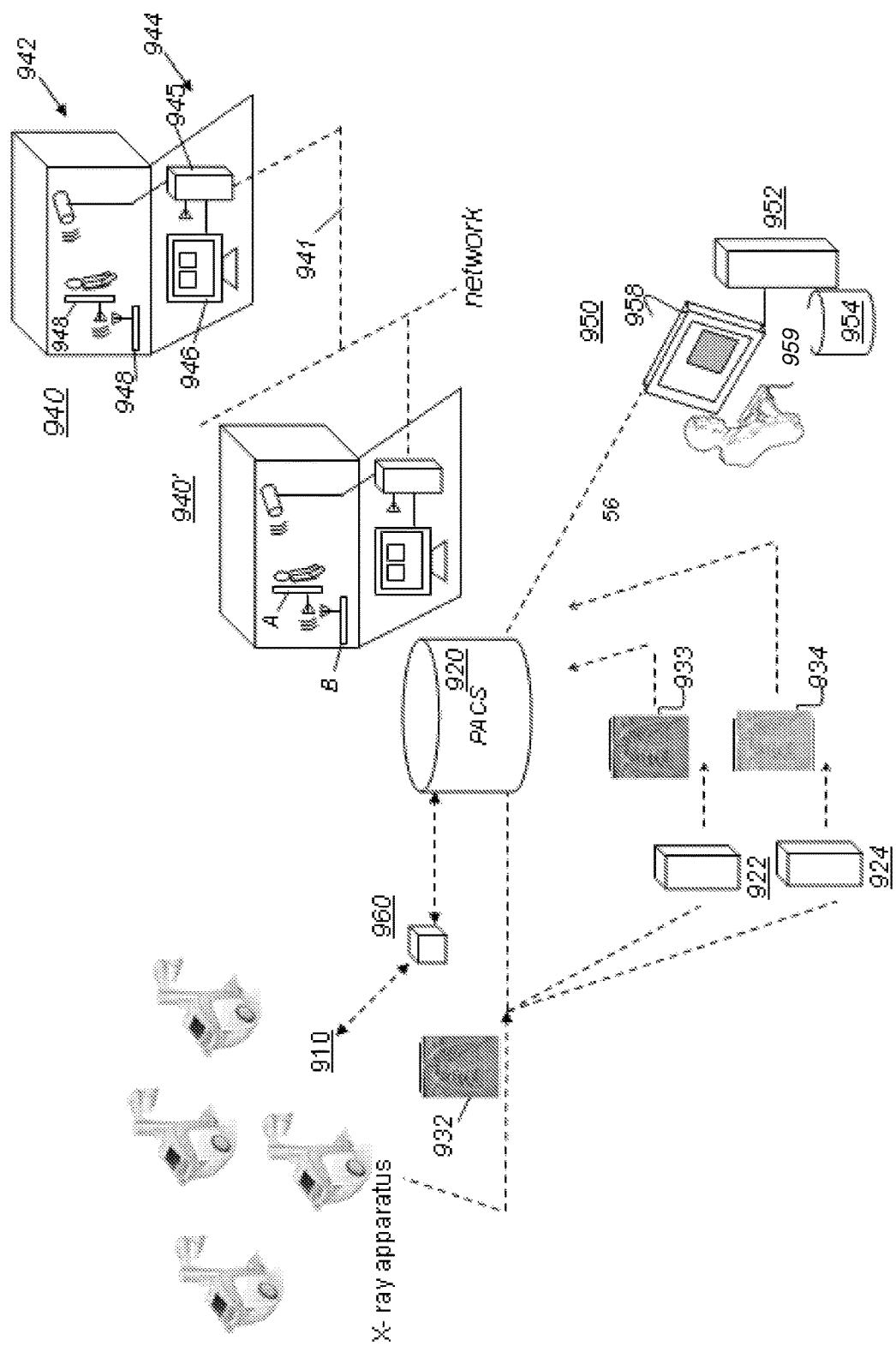
FIG. 9 is a diagram that shows an exemplary relationship of acquisition digital radiographic imaging apparatus (e.g., mobile DR imaging apparatus, x-ray imaging room), reviewing radiographic imaging apparatus, storage radiographic imaging apparatus and/or an image acquisition server.

The schematic diagram of FIG. 9 shows an exemplary relationship of acquisition digital radiographic imaging apparatus (e.g., mobile DR imaging apparatus 910, x-ray imaging room 940), reviewing radiographic imaging apparatus (e.g., workstation at an image management system 950) and/or storage radiographic imaging apparatus (e.g., PACS 920) and shows an overall relationship of a system to an embodiment of a prior image acquisition server 960. As noted previously, a primary image 932 that can be obtained from an image capture by a mobile DR imaging apparatus 910. Primary image 932 can be directly provided for storage in the PACS 920 either as raw or pre-processed image data.

Alternatively, the primary image 932 can be stored at the mobile DR imaging apparatus 910 and provided later to the PACS 920.

As shown in FIG. 9, an image management system 950 coupled to the system can include a logic processor 952, a memory 954, and an operator console that can include a display 958 and an operator entry device 959, such as a keyboard, mouse, touch screen, or other device for entry of operator commands. Commands at image management system 950 provide an additional capability for retrieval, review and/or management of the images stored in the system (e.g., PACS).

Still referring to FIG. 9, also connected to PACS 920 can be one or more X-ray imaging room 940 that can include an imaging room 942 (e.g., a shielded area in which a patient is imaged and containing an x-ray source), and a control room 944 that can include a display 946 and controller 945 for communicating with DR detectors 948 over a wireless interface and containing control logic for supporting and executing imaging operations with a selected DR detector 948. In the embodiment shown, display 946 can be a touchscreen display, enabling the operator or technologist to easily control the X-ray imaging room 940 and select among DR detectors 948 as an active DR detector 948 for obtaining the image using a graphical user interface (GUI). Imaging rooms 940, 940' can be connected to the PACS 920 using a network 941 (e.g., wired, wireless, proprietary, public). Further, a communication network 941 can interconnect the PACS 920 with the mobile DR imaging apparatus 910 (directly or via the prior image acquisition server 960), the prior image acquisition server 960, the x-ray imaging room 940 and/or the image management system 950. The communication network 930 may be wired, wireless, proprietary, or public and comprised of many interconnected computer systems and communication links. Communication links may be hardwire links, optical links, satellite or other wireless communication links, wave propagation links, or any other mechanisms for communication of information.

Primary image 932 can be provided to one or more logic processors 922, 924 that each can perform some type of image processing and analysis operation before the primary images 933 and 934 can be stored in the PACS 920 along with acquired primary image 932. As shown in FIG. 9 the primary image 932 can be pre-processed and suitable for storage/archival as it is provided from mobile DR imaging apparatus 910. It should be noted that, in an alternate embodiment, primary image 932 may be provided as raw data, requiring some amount of processing prior to storage in PACS 920. Logic processors 922 and 924 can generate additional processed secondary images 933 and 934 from raw data or from pre-processed primary image 932, as shown in FIG. 9. In one embodiment, the additional processed secondary images 933 and 934 can be companion images.

In one embodiment, the mobile radiography apparatus 700 (FIG. 8) can be used as one of the plurality of portable DR imaging apparatus 910.

For medical diagnosis, subsequent medical x-ray images can be compared by technicians/doctors/medical personnel to prior medical x-ray images of the same patient. It is preferable that the x-ray images different in time be obtained under the same conditions (e.g., exposure parameters). However, when different equipment, technicians, or medical facilities take the plurality of x-ray images there can be significant differences in the obtained x-ray images.

According to embodiments of the application, prior images can be reviewed before the imaging technician executes a current examination. The technician can "select prior parameters" from a desirable prior image and have a mobile x-ray unit be automatically set to the same parameters as the indicated desirable prior image.

Since prior images can be 10 MBs, 20 MBs, 30 MBs or more of data, and 10, 20 or more than 50 prior images may be related to a current examination, the prior images can constitute a large quantity of data or network traffic to transmit the prior images to the portable DR imaging apparatus 910. Pre-fetching of the prior images can be used to reduce network traffic or to timely provide prior images to the portable DR imaging apparatus 910 for display of a selected prior image. Pre-fetching (e.g., obtaining in advance of their use or need) images can be stored at the portable DR imaging apparatus 910 prior to a technician taking the unit 910 on their "rounds" to capture new/further images. Beneficially, pre-fetching can allow the technician to download the prior images over the wired network (e.g., limited access but faster) compared to a download over the wireless network available throughout the medical facility. The parameters (e.g., kVp level setting) of the pre-fetched prior images can be used to capture the new images for a current exam.

Embodiments of the application can include features of a mobile radiographic unit directed to fluoroscopy imaging.

According to embodiments of the application, the first display 710 and/or the second display 710' (FIG. 8) can provide prior images capabilities/functionality to the mobile radiography apparatus 700 such as but not limited to: (i) loading priors (e.g., previously captured image(s)) for a mobile imaging x-ray system; (ii) loading priors wirelessly or when directly connected to a network or image storage system (e.g., PACS 920); storing priors as full images or as a sub-sampled image to reduce disk space.

According to embodiments of the application, the first display 710 and/or the second display 710' can provide prior image display" feature/GUI with capabilities/functionality such as but not limited to: (i) display of a prior image itself; (ii) determining the size of the lung field in the image or determining prior image orientation (e.g., landscape vs. portrait) and determining for the same whether the user wants/selects consistent detector location & orientation between images, or the user indicates the prior was inadequate and a change should be made; (iii) displaying exposure technique information; (iv) matching current exposure techniques with prior images; (v) displaying SID (Source to Image Distance); (vi) matching SID with prior images; (vii) displaying angle measurements such as but not limited to patient angle—supine, upright or some angle in-between, X-Ray tube angle, X-Ray tube angle to patient angle—usually 90 but not always; (viii) matching angle with prior angle; (ix) displaying grid information such as but not limited to: was a grid used, grid ratio, transverse vs. longitudinal, recommended SID/SID range for that grid; (x) matching grid/no-grid and grid type with the prior; (xi) showing the prior exposure index to indicate if too much or too little exposure was used in the prior image; (xii) consistent rendering between prior image and new one (e.g., see below); (xiii) image capturing device or detector for the prior image (e.g., manufacturer, model, device name, etc.). There are variations in the quality (e.g., ISO speed, sensitivity) of detectors (e.g., better detectors require less dose) and also variations in the method different manufacturers use to calculate Exposure Index. Thus, knowing the image capturing device can benefit the technician.

Certain exemplary system and/or method embodiments described herein can provide fast frame-rate wireless cassette-sized x-ray image detectors powered by an internal battery. Mobile x-ray acquisition control system and/or method embodiments can be configured with a wireless cassette-sized x-ray image detector that is capable of capturing x-ray images at a rapid frame rate. Generally, the term fast or rapid frame-rate x-ray imaging is used herein instead of fluoroscopy because exemplary radiographic acquisition can serve a more general purpose, e.g. dual energy, tomosynthesis, fluoroscopy, and the like. Certain exemplary embodiments described herein can provide mobile x-ray acquisition control systems that use a rigid c-arm or other support arm where the detector is detachable. In one embodiment, when detector is detached, the c-arm unit's detector arm is removable or the c-arm unit's detector arm retracts into the upper arm or housing of the unit.

Certain exemplary embodiments described herein can provide in-room x-ray acquisition control system capable of fast frame-rate x-ray imaging with a wireless x-ray image detector. Additional exemplary embodiments described herein can provide an x-ray acquisition control system comprising a portable, e.g. hand-held, x-ray tube/generator, a wireless x-ray image detector and a tube/generator mounting mechanism that enables the tube to be aligned with the detector.

In one embodiment, x-ray sources on the acquisition control system may provide continuous or pulsed operations. In one embodiment, x-ray image detector can be used while docked (e.g., not detached) to an acquisition control system. In one embodiment, a docked x-ray image detector can connect to a port that: supplies power to the detector; charges the battery in the detector; enables wired communication between the detector and the acquisition control system; enables transmission of data between the detector and the acquisition control system; or any combination of the above embodiments. Alternatively, an x-ray image detector may be tethered to the acquisition control system.

In one embodiment, an acquisition control system has a means to manually align the x-ray source (tube assembly) to the x-ray image detector using visual feedback means or audio feedback means. In one embodiment, the acquisition control system and x-ray image detector are configured with devices to enable relative geometric measurements to be made, e.g. source to detector distance, the angles between the normal of the detector and the primary x-ray beam. The acquisition control system can also include a means to automatically align the x-ray source to the x-ray image detector. Alignment is not restricted to perpendicular configuration, but includes x-ray impingement at various angles with respect to the axes of the detector.

Certain exemplary system and/or method embodiments can provide acquisition control that can automatically select the appropriate x-ray source from an array of x-ray sources and to align the activated x-ray source to achieve the desired projection angle. (This can negate the need for physical motion of the x-ray source). Alignment is not restricted to perpendicular configuration, but includes x-ray impingement onto the x-ray image detector surface at various angles with respect to the axes of the detector. In one embodiment, exemplary acquisition control systems can have the ability to automatically collimate (e.g., symmetric or asymmetric) the x-ray beam in order to restrict the emitted beam to the surface area of the detector.

In one exemplary embodiment, there is a switch that operates the acquisition control system. Engaging the switch initiates the rapid frame-rate imaging process.

Certain exemplary system and/or method embodiments can provide an AEC/ABC whose functionality is derived from the pixel data in the raw image, a sub-region of the raw image, a sub-sampling of the raw image; the AEC functionality is derived from dedicated radiation sensors that are integral to the pixel substrate but different in design from the pixel imaging sensors; the AEC functionality is derived from x-ray sensors internal to the detector housing but separate from the pixel substrate (e.g., a thin ion chamber placed inside the detector housing); the AEC functionality is derived from a sensor that snaps onto the exterior of the detector.

Exemplary system and/or method embodiments can include an x-ray grid that may be attached onto the x-ray image detector. The grid can be configured with a physical or electronic marker that can be identified and recognized by the acquisition control system. The identifying information, along with geometric information (SID, angulations, etc) can be used by a component of the acquisition control system to ensure the x-ray source is properly aligned with the grid before the x-ray source can be fired. Proper alignment of the system may be a visual or audio signal. Certain exemplary embodiments can provide x-ray image detectors configured with a phase lock synchronization mechanism that can synchronize the exposure integration and image signal readout from the detector when the x-ray source is pulsed.

In one embodiment, a x-ray image detector stand can be included that is configured with a physical or electronic marker that can be identified and recognized by the imaging system. The identifying information, along with geometric information (SID, angulations, etc) is used by a component of the acquisition control system to ensure the x-ray source is properly aligned with the detector before the x-ray source can be fired. The component can be a visual or audio signal. One exemplary acquisition control system can be configured with independently movable collimator blades.

Certain exemplary acquisition control system and/or method embodiments can be configured with temperature sensors that monitor the temperature of the x-ray tube assembly and the x-ray image detector. In one embodiment, temperature readings and the x-ray techniques can be used to provide feedback to the user of how much longer the system can be used before it will be shut-down in order to avoid overheating. In one embodiment, x-ray image detectors can be configured with a temperature sensor and the temperature information can be used to adjust the gain-offset calibration algorithm.

Certain exemplary acquisition control system and/or method embodiments can be configured with multiple x-ray sources. Exemplary x-ray sources shall be interchangeable and have the ability to be quickly changed out in the case that the current x-ray source nears an overheated state. In another exemplary embodiment, the x-ray sources may rotate in a queue to avoid overheating. Preferably, when the x-ray sources are changed, the new x-ray source has a focal spot that is of the same size and alignment as the previous x-ray source. Certain exemplary embodiments provide redundancy (e.g., multiple x-ray assemblies) in long imaging procedures where the x-ray source is left on for long periods of time. In one embodiment, before use, the x-ray sources can be put through a tube warm up procedure. Exemplary imaging systems an/or methods can perform rapid-frame rate dual-energy imaging.

Certain exemplary acquisition control system and/or method embodiments can accept an integrated injecting system, e.g. an x-ray contrast injector. The injecting system can be synchronized with the rapid frame-rate exposures to adapt, simplify or optimize the procedural workflow.

Certain exemplary acquisition control system and/or method embodiments can accept an integrated ultrasound imager. The imaging system can provide rapid frame-rate x-ray imaging with registration and fusion with the ultrasonic imagery.

Certain exemplary acquisition control system and/or method embodiments can include the ability for a user to define an ROI on the x-ray image detector. Rapid frame-rate imaging readout can be performed exclusively on the ROI. In another embodiment, the rapid frame-rate imaging readout can be performed on both ROI and non-ROI regions, but with a different frame-rate in the non-ROI region. In one embodiment, an ROI can be physically obtained with independently movable collimator blades; the ROI may be realized on different stops of a rotating wheel that is composed of distinct regions composed of material having different radiolucency; the ROI may be realized using a continuously rotating wheel that is composed of materials having different radiolucency and that is synchronized with pulsed x-rays.

Certain exemplary acquisition control system and/or method embodiments can be configured with a synchronized contrast bolus injector that has the ability to center the x-ray source, or field of view, over the bolus injection site and to collimate the x-ray source to the x-ray image detector, or field of view; the acquisition control system has the ability to capture a diagnostic quality radiograph (i.e. a key image) when the bolus attains a specific state (e.g. the bolus reaches a specific location, or the bolus contrast has reached a plateau within the image frame, or the like). In one embodiment, acquisition control systems, configured with a synchronized contrast injector, can provide that ability to automate the acquisition of a DSA by using a lower dose setting until the desired contrast is reached within the ROI (e.g., which may be the entire detector) and to provide the ability to stop live imaging when there is less than a target amount of contrast remaining in the ROI.

Figure 10:
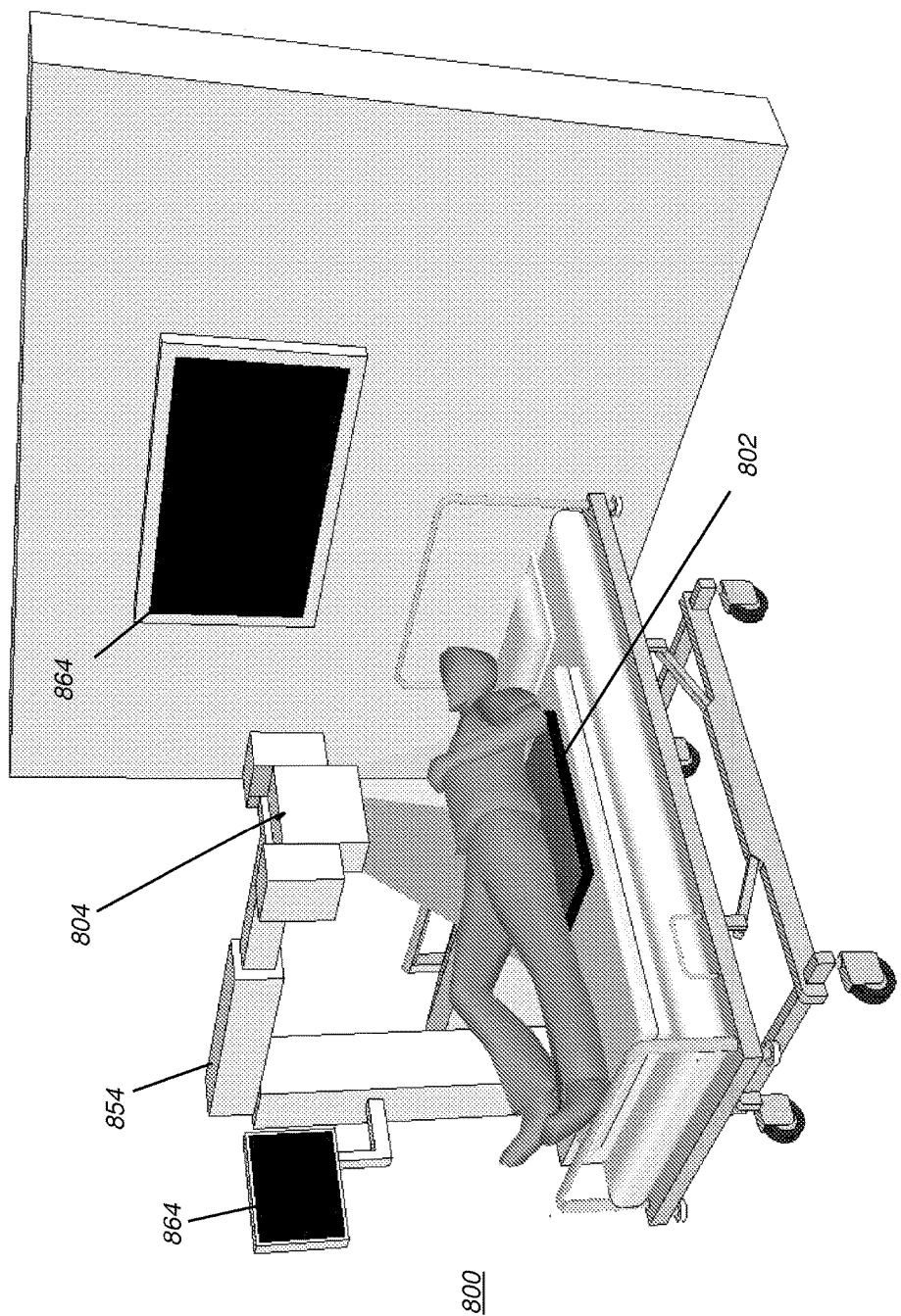
FIGS. 10-14 are diagrams that show fluoroscopic imaging apparatus embodiments according to the application.
Figure 11:
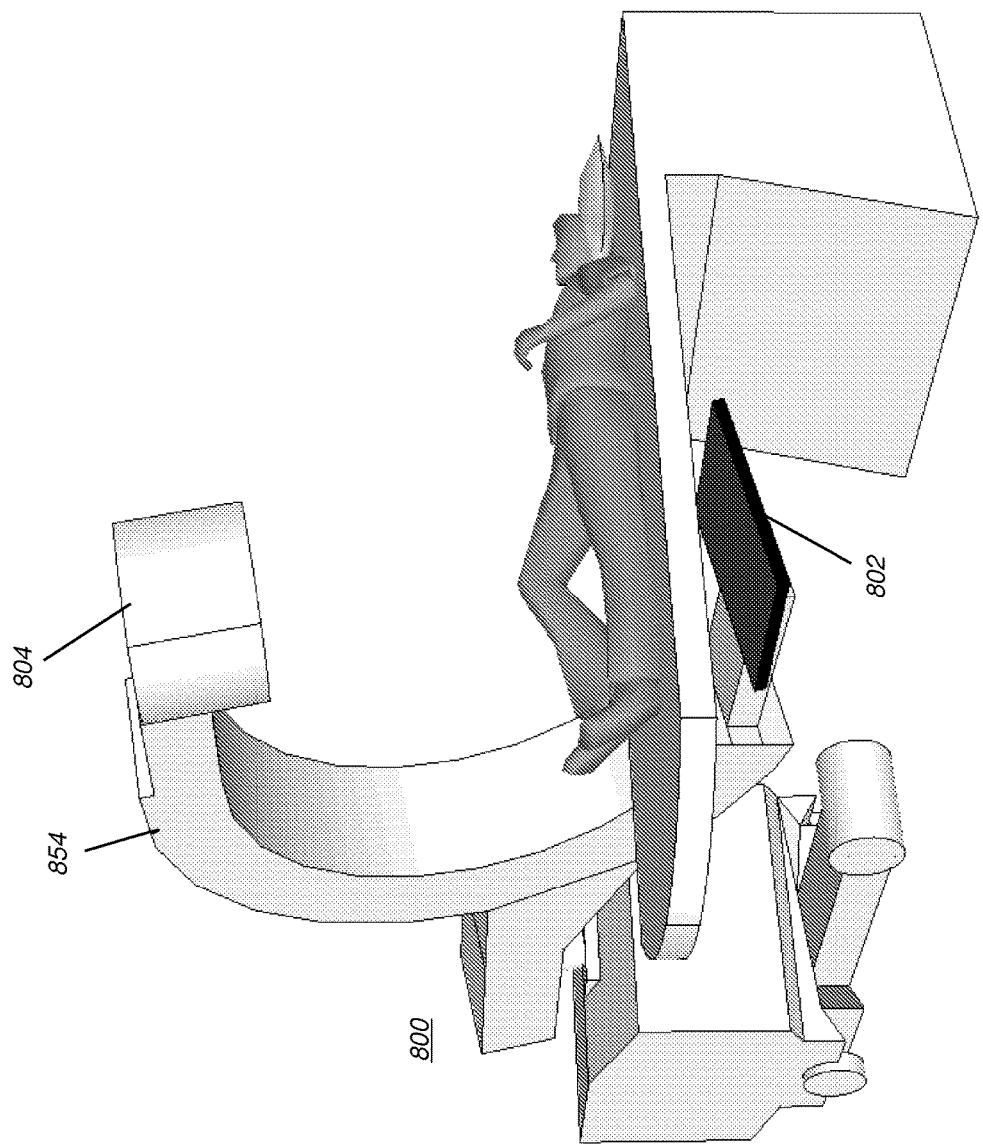
Figure 12:
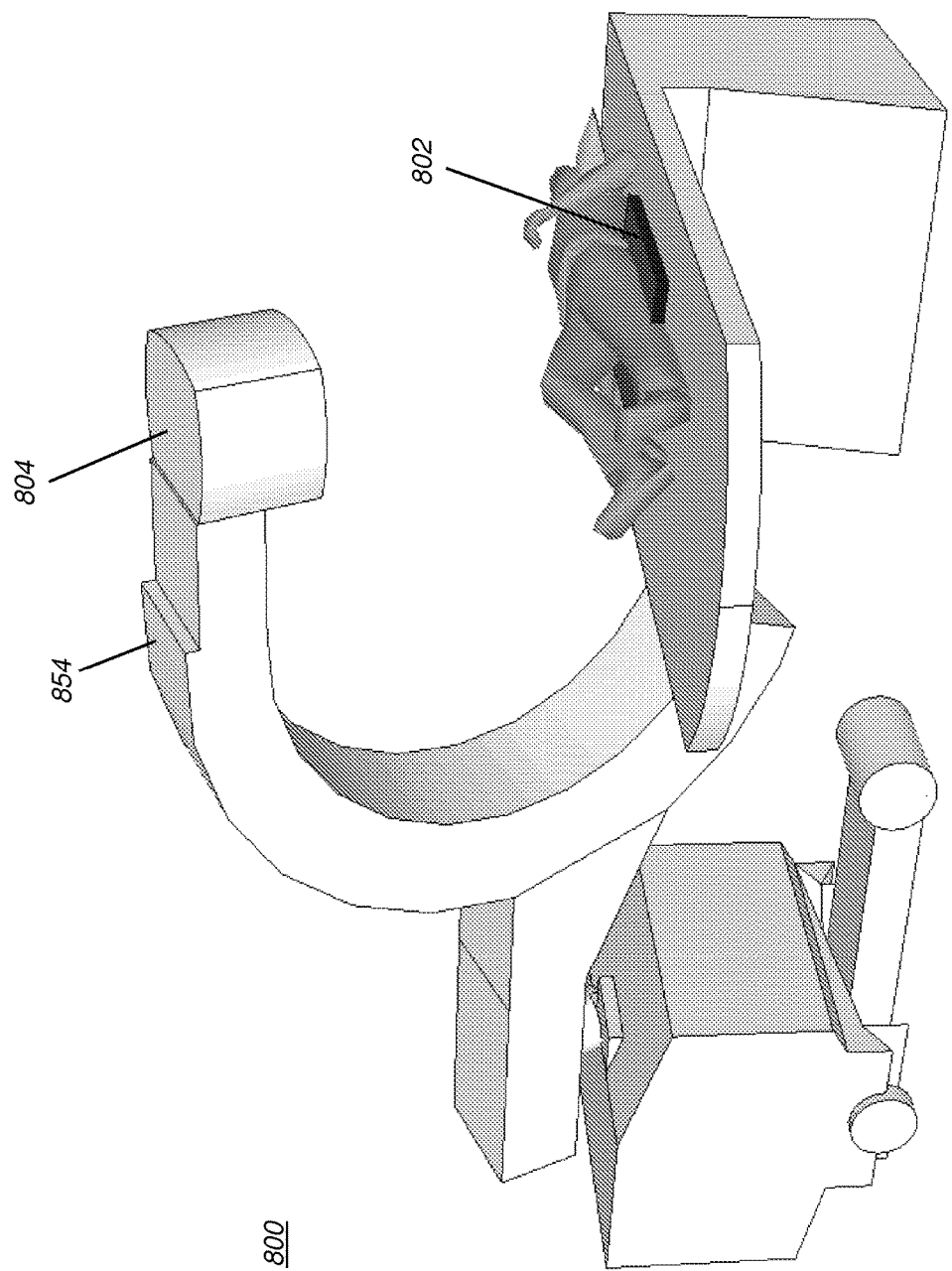
Figure 13:
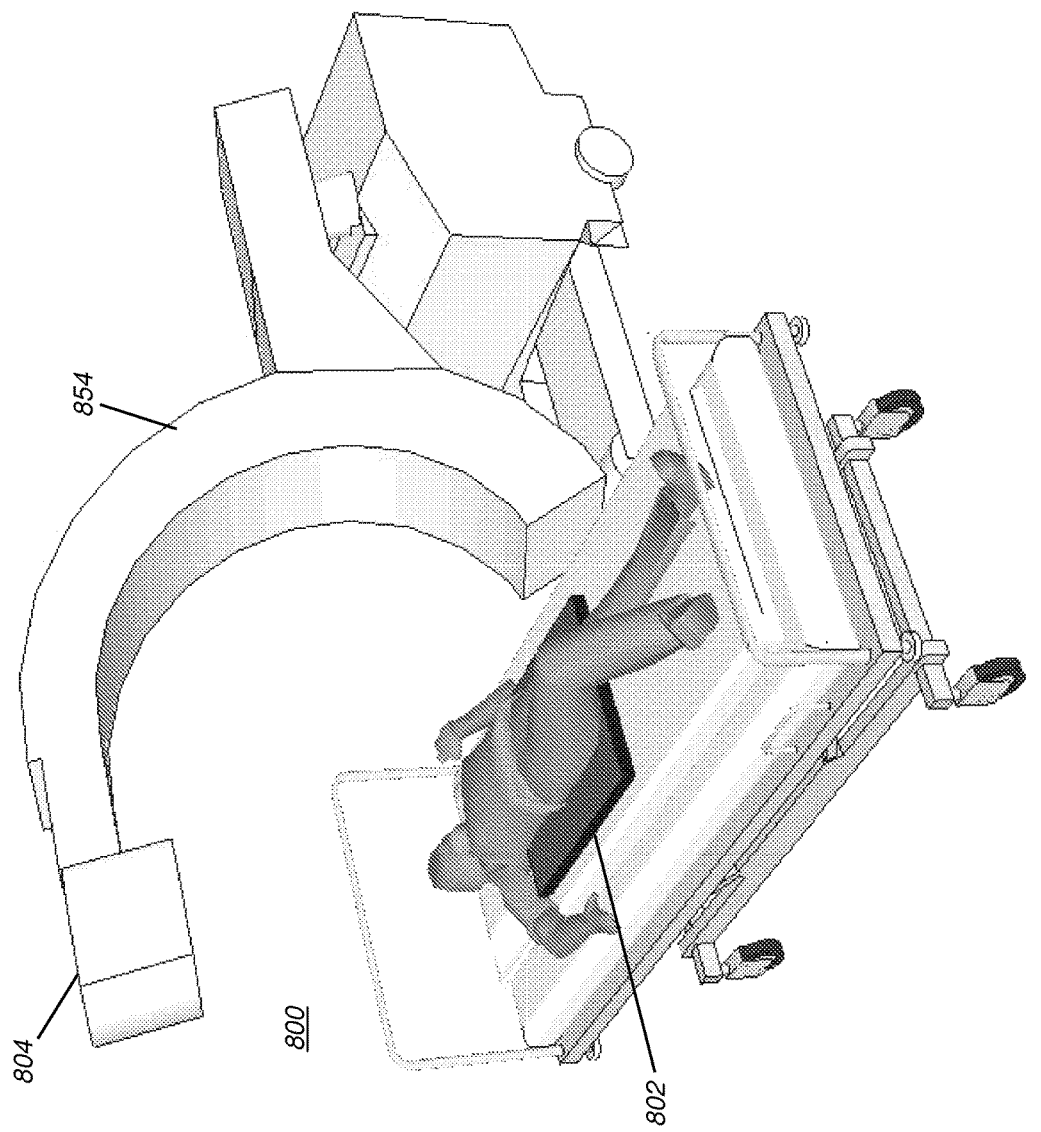
Figure 14:
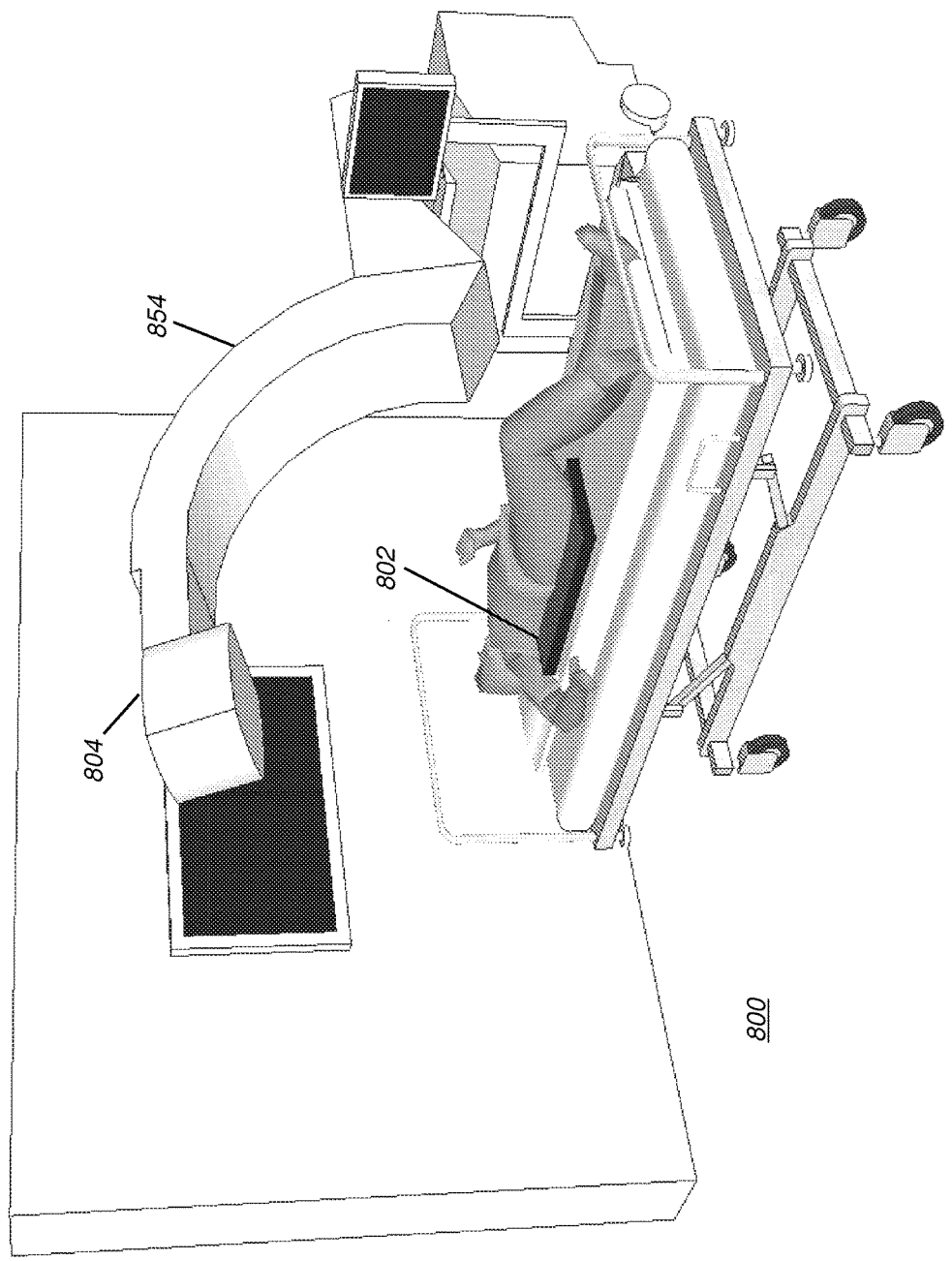

FIG. 10 shows a fluoroscopic imaging apparatus 800 according to the present disclosure. A support arm 854 supports x-ray radiation source 804 for directing radiation through a subject, such as a patient, and toward an imaging detector 802. One or more displays 864 are provided for display of images that are acquired. FIG. 10 shows detector 802 in a free-standing arrangement. FIG. 11 shows an alternate imaging apparatus 800 with detector 802 supported on a C-arm as one exemplary type of support arm 854. FIGS. 12, 13, and 14 show an alternate imaging apparatus 800 with a C-arm support arm 854 and a free-standing detector 802.

FIG. 15 is a diagram showing exemplary applications of fluoroscopic imaging apparatus and related imaging apparatus that use C-arms.

FIG. 16 is a diagram showing exemplary capabilities of a digital portable flat panel-type radiographic detector (e.g., for use with fluoroscopic imaging apparatus) according to certain exemplary embodiments of the application.

In the context of the present disclosure, the term "orthogonal" or "normal" is used to describe an angular relationship of about 90 degrees+/−10 degrees or, alternately, 270 degrees+/−10 degrees. The term "parallel" describes an angular relationship of about 0 degrees, +/−10 degrees or, alternately, 180 degrees, +/−10 degrees. Angles outside these values and thus in the range from about 10 degrees to about 80 degrees are considered to be oblique.

Positive Beam Limitation

Conventional C-arm systems for fluoroscopy and for radiographic imaging in general have applied various techniques to the problem of limiting the shape of the radiation beam that passes through the subject and is incident on the imaging detector. A desired outcome of this feature, termed "positive beam limitation" is to restrict the shape of the radiation beam so that patient exposure is constrained to a region of interest (ROI) that does not exceed the bounds of the imaging detector.

For fixed-geometry imaging apparatus, calculations and methods for achieving positive beam limitation is relatively straightforward. Simple trigonometric relationships allow the shape of the beam relative to the detector to be readily calculated when the beam is directed orthogonally to the imaging detector, such as in a conventional C-arm fluoroscopy system.

Imaging apparatus having free-standing imaging detectors, as shown in FIG. 10, for example, can be significantly advantaged over fixed-position C-arm systems, in some cases allowing imaging that would otherwise be very difficult to achieve, or very awkward or uncomfortable for the patient. For imaging apparatus that employ a free-standing imaging detector 802, however, the task of achieving positive beam limitation is considerably more complex. It may not be possible or desirable to position the free-standing imaging detector so that the radiation beam is orthogonal to the detector. The conventional collimator has light blocking blades or similar features that are typically arranged at integer multiples of 90 degrees relative to each other or are arranged to define a circular aperture. This conventional collimator arrangement allows positive beam limitation to be readily calculated and obtained where the central axis of the emitted beam is orthogonal to the detector; however, this cross-sectionally orthogonal beam shape can be clipped by the edge of the detector when the angle of incidence is at an oblique angle, allowing excess radiation beyond the outline of the detector, or constraining the beam to only a small portion of the detector.

Embodiments of the application address the problem of providing positive beam limitation by sensing the position of the imaging detector relative to the radiation source, adjusting the collimator or other aperture in the path of the radiation beam to shape the beam for incidence on the detector or, more generally, on a predetermined area of the detector, and then energizing the radiation source to emit the shaped radiation beam through the subject and onto the imaging detector for acquiring image data. Exemplary methods of embodiments of the application can be advantageous for imaging modes such as fluoroscopy, where the use of a free-standing detector is preferred for reasons such as for patient comfort, for reducing the need for specialized support equipment, or for improved visibility for the practitioner, for example.

Figure 17:
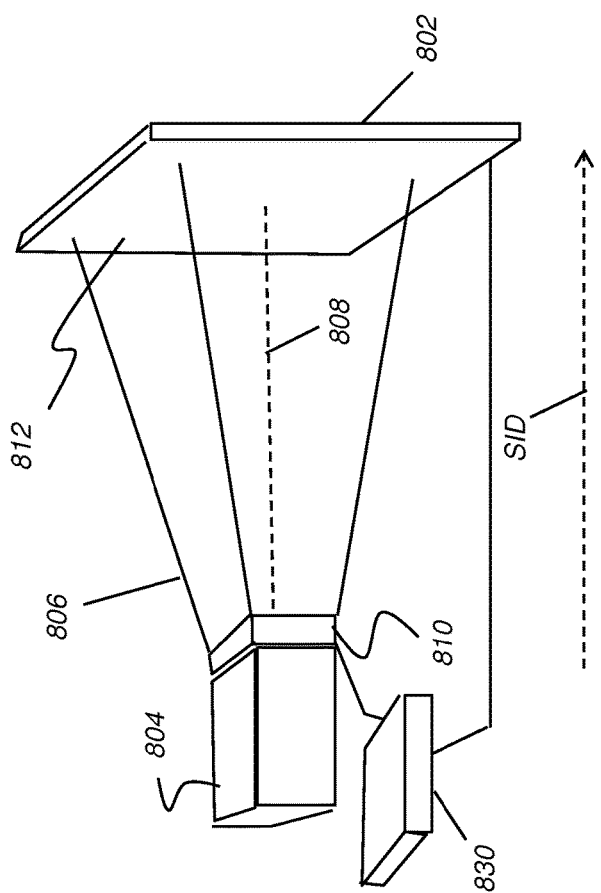
FIG. 17 is a schematic block diagram that shows some of the dimensional and angular relationships of interest for determining the position of an imaging detector that is orthogonal relative to a radiation source.

The schematic block diagram of FIG. 17 shows some of the basic dimensional and angular relationships that are of interest for determining the position of an imaging detector 802 that is orthogonal relative to a radiation source 804. With conventional fixed-position C-arm imaging apparatus, a source to image distance SID is a constant determined by the dimensions of the C-arm. Radiation beam 806 has a central axis 808 that corresponds to the center of the beam 806 as it emerges from the collimator or other aperture 810. Collimator or aperture 810 shapes the beam cross-sectionally, for incidence on a predetermined area 812 of imaging detector 802. A processor 830 that is in signal communication with detector 802 and with collimator 810 adjusts the collimator 810 blades in order to provide a suitable aperture for the desired x-ray beam emitted from source 804. In conventional practice, collimator or aperture 810 provides a beam 806 that is rectangular in cross section. This beam shape is compatible with the projected profile of imaging detector 802, considered at an orthogonal along central axis 808.

Figure 18:
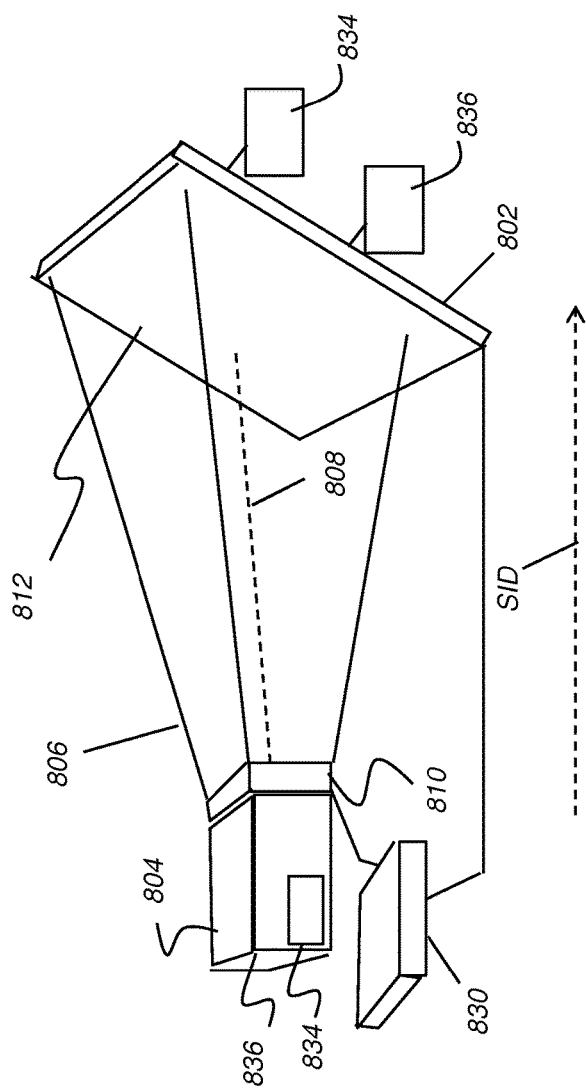
FIG. 18 shows dimensional and angular relationships that are of interest for determining the position of an imaging detector that is at some oblique angle relative to a radiation source.

The schematic block diagram of FIG. 18 shows dimensional and angular relationships that are of interest for determining the position and orientation of an imaging detector 802 that is at some oblique angle relative to a radiation source 804. Here, knowing source to image distance SID is useful along with other angular variables. Because central axis 808 is oblique with respect to the imaging detector 802 surface, detector 802 no longer appears to be rectangular, so that beam 806 must have a non-rectangular cross-sectional shape in order to fit fully onto detector 802 without extending beyond edges of detector 802. Processor 830 controls an adjustable collimator to perform this function, as described in more detail subsequently.

Figure 19:
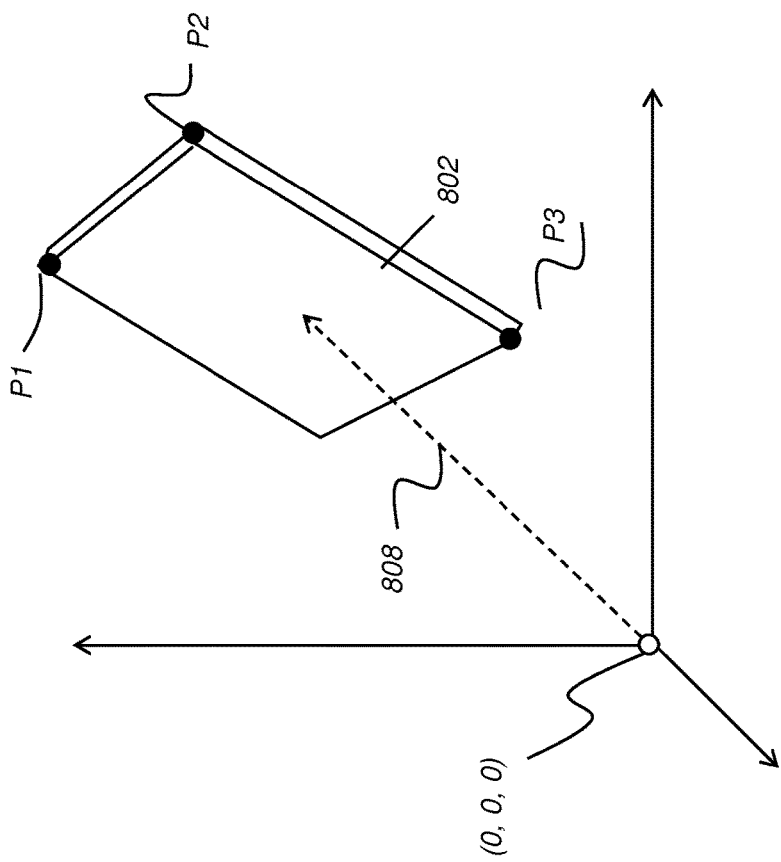
FIG. 19 shows a schematic diagram of three-dimensional coordinates for a digital x-ray detector relative to a radiation source at the origin.

In terms of the familiar Cartesian coordinate system for 3-D positioning, radiation source 804 can be considered to be the origin, with coordinates (0, 0, 0), as shown in FIG. 19. In one embodiment, for example, identifying coordinates of at least three additional corner points P1, P2, and P3 can provide the relative position and orientation of detector 802.

Figure 20:
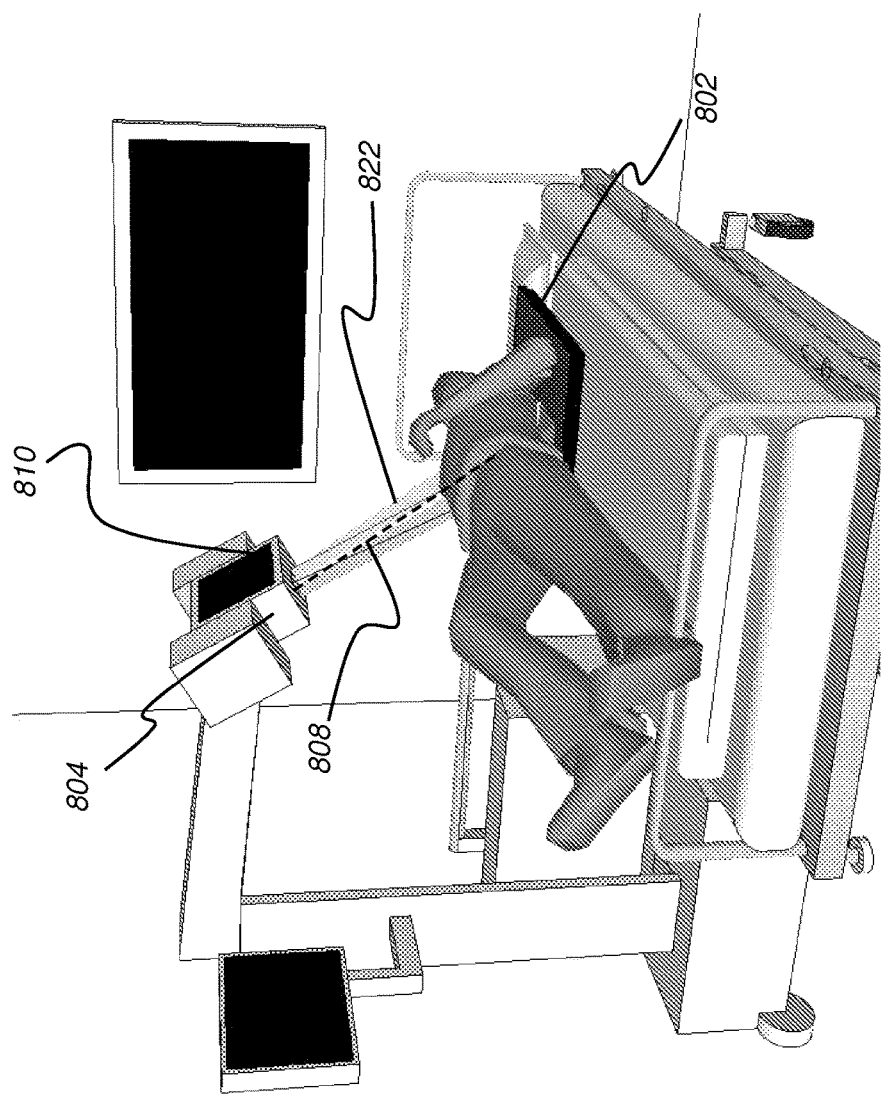
FIG. 20 shows use of an initial measurement beam according to an embodiment of the present invention.

There are a number of different techniques for accurate detection of free-standing detector 802 position and the locations of corner points P1, P2, P3 that also indicate orientation, as well as other detector features relative to source 804 when detector 802 is positioned behind the patient or other subject. According to an embodiment of the application, shown in FIG. 20, after the detector 802 is placed in its position, an initial measurement beam 822 is emitted and directed toward the subject and detector 802. The measurement beam 822 is at a fluence level, where fluence relates to x-rays per unit area (or dose level such as in mR or mGy), that is less than 50% of that of the fluence of the emitted shaped radiation beam that is used for imaging, such as at 25% or 15% or less of the imaging fluence level, for example. The measurement beam is also at a higher energy level (expressed in kVp) that is at least 15% higher than that used for imaging to provide lower patient dose. The position of collimator blades is known, so that a predetermined beam shape defined by this aperture is used for the measurement beam 822. The collimator shadow is then obtained from the detector 802. Conventional image segmentation techniques are used to identify coordinates of image pixels on detector 802 that correspond to one or more corners or edges of the detected beam. Such measurement beam information on collimator settings and beam edge detection can give sufficient information about the area of measurement beam incidence for calculating the central axis of the emitted beam. Information on the relative angle of detector 802 from orthogonal relative to the beam central axis 808 can be calculated using shape information obtained from the image segmentation. The relative amount of "keystoning" and other shape information give sufficient data for position and orientation calculation, using transformation matrices, for example.

Still other approaches for accurate detection of free-standing detector 802 position and the locations of corner points P1, P2, P3 utilize a pattern of signals that are transmitted between locations on detector 802 and processor 830. Signals for positioning can be transmitted by processor 830, by collimator 810, or by transmitter circuitry that is coupled directly to detector 802. The signals can be wireless signal types, such as audio or radio-frequency (RF) signals. According to an alternate embodiment of the application, tilt sensors or accelerometers are coupled to detector 802 and used for position sensing. According to another alternate embodiment of the application, global positioning system (GPS) components are used to provide signals to processor 830 for detector 802 position sensing and reporting. Any of a number of possible arrangements of sensing element 834 or one or more transmitter elements 836 can be used and sensing elements 834 and transmitter elements 836 can be optionally coupled to the collimator 810, to detector 802, or to both, as indicated in FIG. 18.

Positive beam limitation uses the positional information obtained from detector 802 and the capability to control the shape of the aperture 824 from collimator 814 or 820 to shape the emitted radiation so that shaped emitted radiation is sufficient for or best suits particular clinical or diagnostic goals, including use in fluoroscopy and other imaging modes that obtain one or more radiographic images during an imaging session. In some cases, this entails constraining radiation to a portion of the detector 802 that provides images of a region of interest (ROI); in other cases, this entails constraining radiation so that it matches or closely approximates the outline of the detector 802 or does not exceed the outline of the detector along any edge of detector 802; in still other cases, this entails constraining radiation so that the full detector is exposed.

Figure 21:
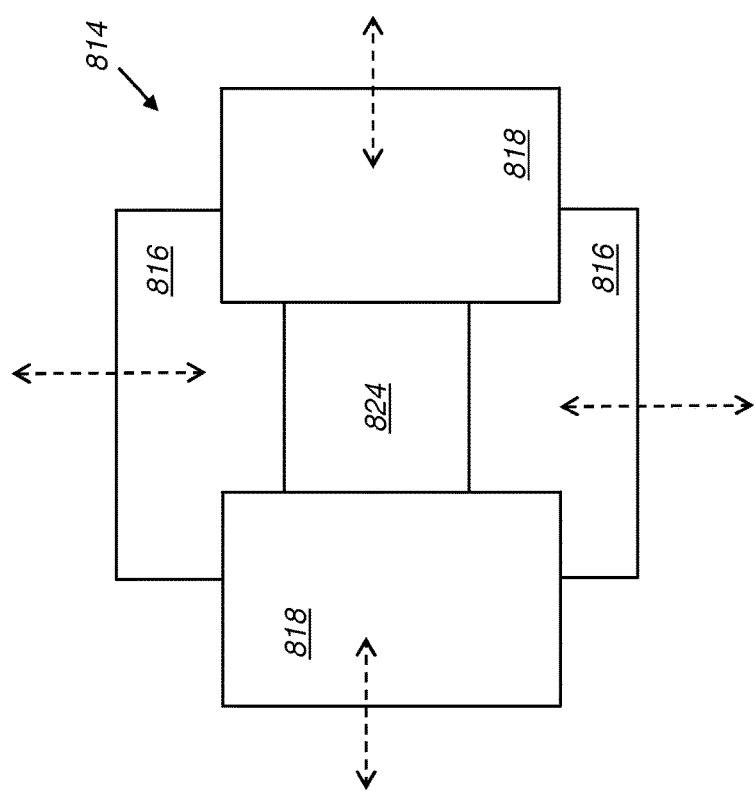
FIG. 21 shows an arrangement of a conventional collimator for obtaining a beam having a rectangular cross section.

The schematic diagram of FIG. 21 shows an arrangement of a conventional collimator 814 for obtaining a beam having a rectangular cross section. Orthogonally disposed blades 816 and 818 are moved into place, along the indicated directions, to define an aperture 824 through which the radiation is emitted to provide the shaped beam. Blades 816 and 818 are formed of lead or other suitable radiation-absorbing material. In one embodiment, individual blades of the disposed blades 816, 818 can be separated moved (and monitored).

Figure 22:
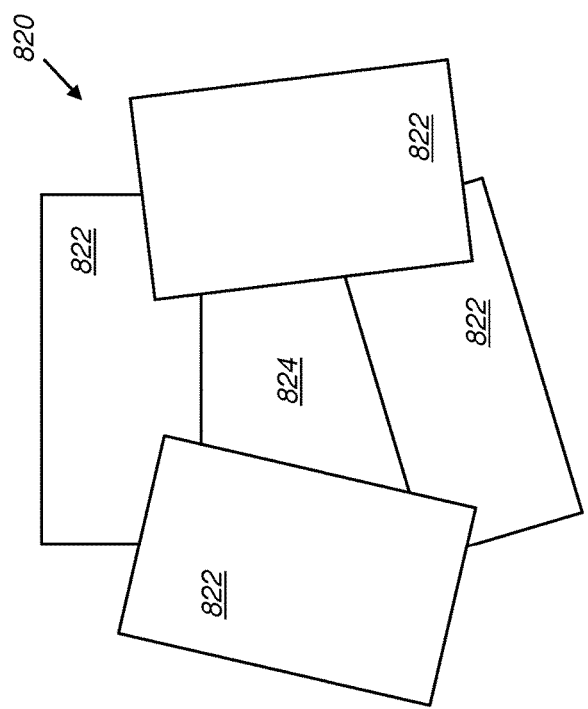
FIG. 22 shows an arrangement of a collimator for obtaining a beam having a rectangular or non-rectangular cross section.

The schematic diagram of FIG. 22 shows an arrangement for a collimator 820 according to an embodiment of the application. Collimator 820 has blade segments 822 that are independently adjustable and movable over a range of angles to allow aperture 824 to be non-rectangular in shape and non-symmetrical about a central axis. The embodiment shown in FIG. 22 can allow the cross-sectional shape of the emitted beam to be other than rectangular so that it can conform or better conform to the projected profile of the detector 802 relative to the radiation source 804. Other methods for obtaining non-rectangular apertures using an adjustable collimator are described, for example, in U.S. Pat. No. 7,340,032 to Besson.

Figure 23:
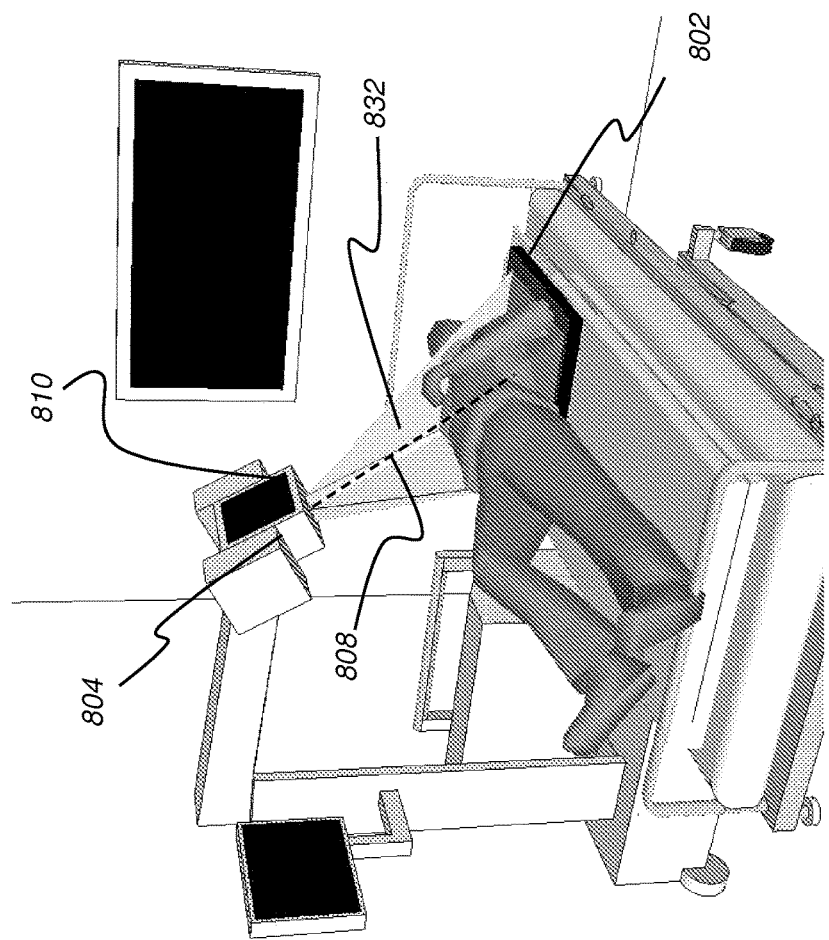
FIG. 23 shows positive beam limitation constrained to the detector surface dimensions.
Figure 24:
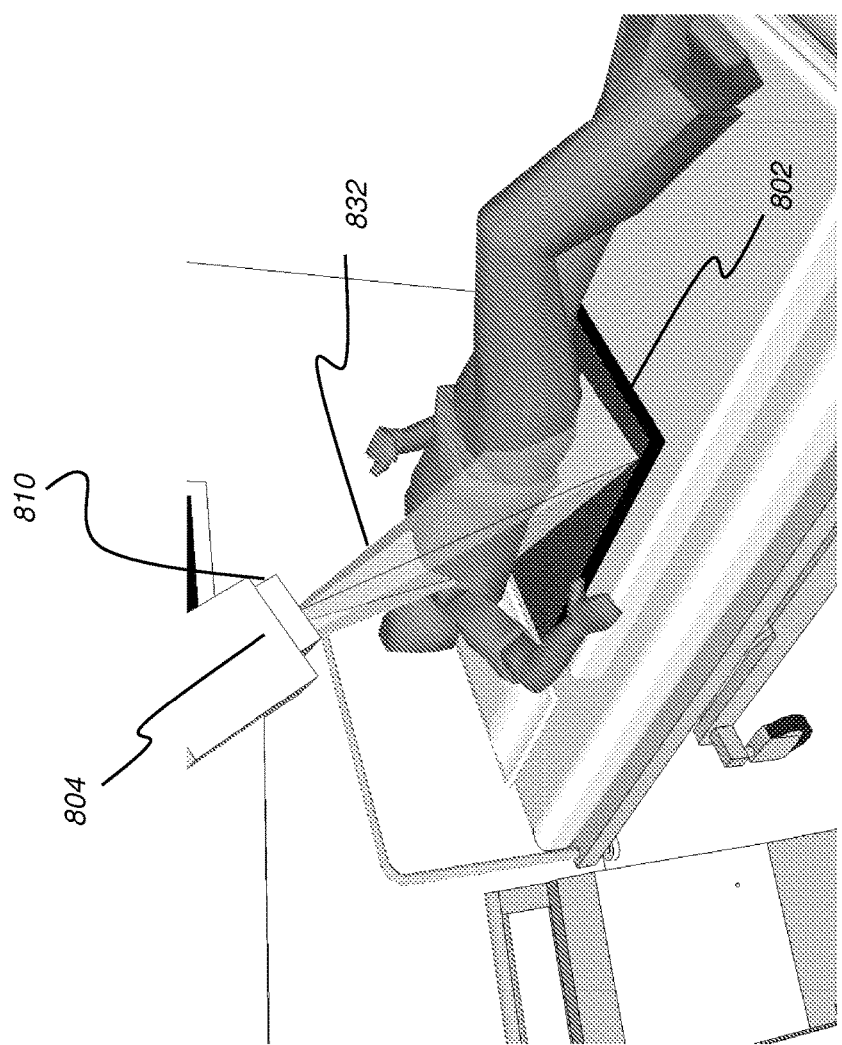
FIG. 24 shows positive beam limitation constrained to an ROI within the detector.
Figure 25:
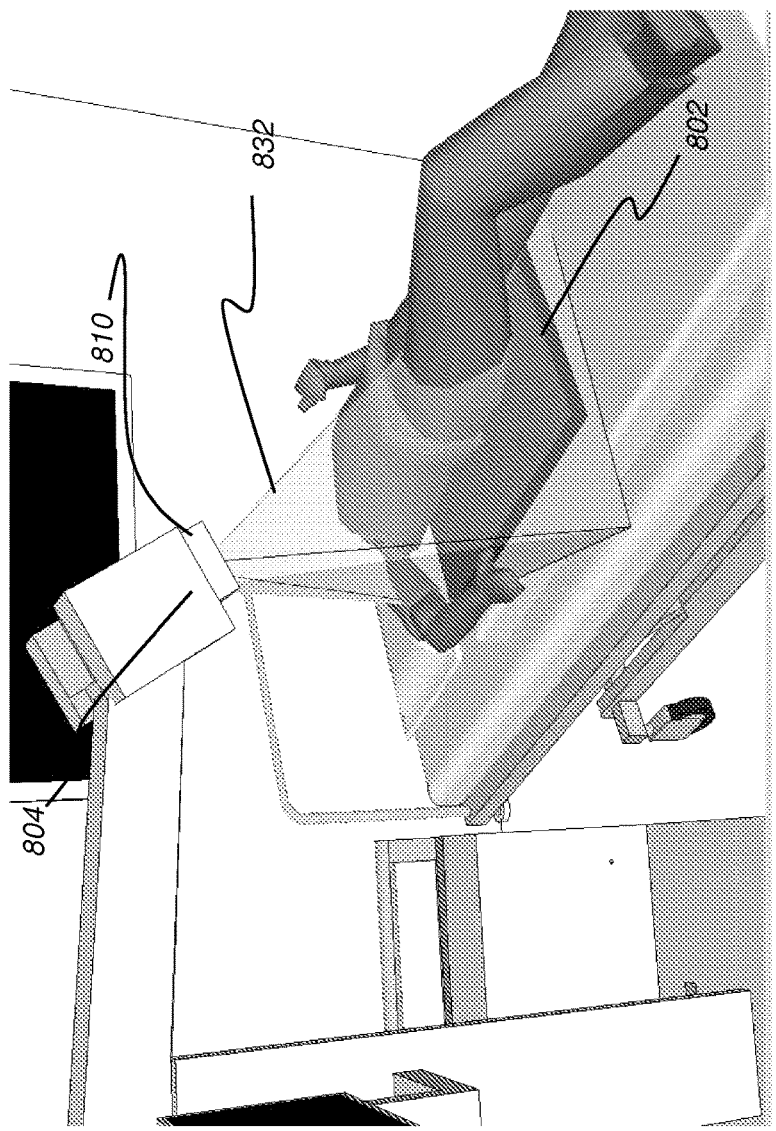
FIG. 25 shows positive beam limitation for imaging the full detector with radiation from an oblique angle.

FIGS. 23, 24, and 25 show how selected positive beam limitation embodiments can be applied in some of the different cases described, with the x-ray beam emitted at an oblique angle with respect to the detector 802 surface. In FIG. 23, an emitted beam 832 is at an oblique angle relative to detector 802 and the beam 832 shape is constrained to the shape of the detector 802 surface. Where an oblique angle is used, some ability to adjust the shape of aperture 824 for a non-rectangular beam, as shown and described with respect to FIG. 23 is typically used.

In FIG. 24, the emitted beam 832 shape is constrained to a region of interest that lies within the detector 802 surface. Either the aperture described with reference to FIG. 23 or that described with reference to FIG. 24 can be used when imaging an ROI in this way. In one embodiment, a prescribed margin (e.g., adjustable in size based on exam type, SID, imaging areas environmental conditions, spectrum or the like) can be enforced between the emitted beam 832 and an edge of an area of detection provided by the detector 802.

FIG. 25 shows an alternate case in which beam 832 can exceed the imaging area of detector 802 but provides a beam shape that images using the complete pixel array of detector 802.

When radiation is directed to the detector 802 at an oblique angle, as was shown in FIG. 18, the energy profile of the emitted radiation beam 832 changes from that provided in orthogonal incidence of the beam as in FIG. 17. This is because the beam intensity is reduced by the inverse square of the distance; with respect to FIG. 18, this means that, in the absence of a subject being imaged or with respect to the beam itself, the amount of energy received along the top of the detector 802 surface is less than the amount of energy received lower along the surface of detector 802. For this reason, certain exemplary embodiments can implement additional calibration used to adjust for non-orthogonal angular disposition of detector 802. For example, gain tables used in processing the raw image data received at detector 802 can be adjusted for angular incidence.

Retractable C-Arm and Detachable Detector

Figure 27:
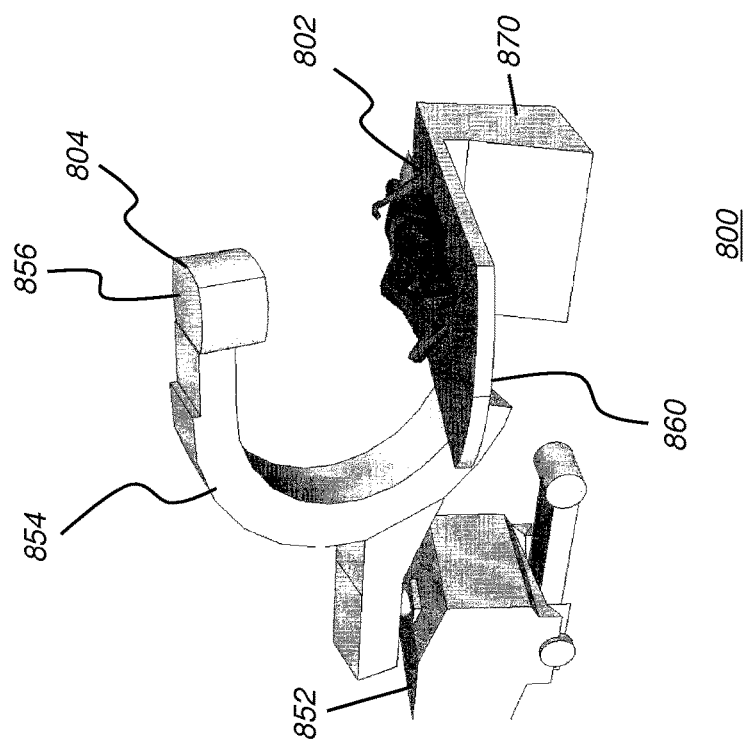
FIG. 27 shows the portable imaging apparatus having its C-arm in the retracted position, with the imaging detector detached.
Figure 26:
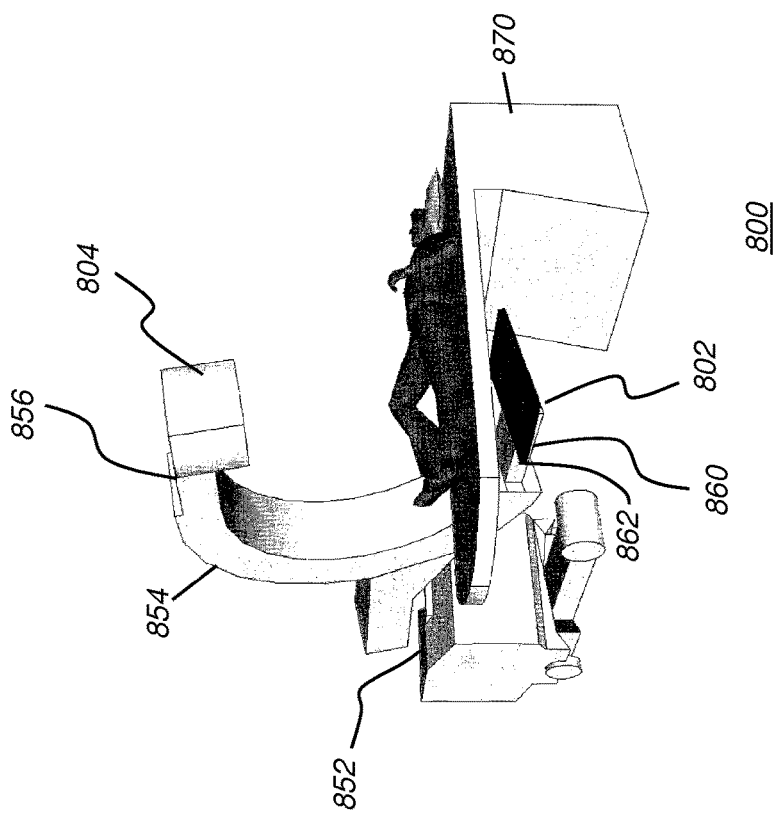
FIG. 26 shows a portable imaging apparatus that has a C-arm with its retractable arm in extended position.

As shown in FIGS. 26 and 27, portable fluoroscopic imaging apparatus 800 has support arm 854, shown as a C-shaped support arm 854 in this particular embodiment, mounted on a transport frame 852. Support arm 854 rotates over a range of angles. Support arm 854 has a fixed end 856 that is coupled to radiation source 804 and a retractable end 860 that has a support 862 that seats imaging detector 802 in a removable manner. Detector 802 is detachable from support 862 and support 862 retracts into retractable end 860 of support arm 854 as shown in FIG. 27. Detector 802 is then usable for free-standing operation, such as placed beneath or alongside the patient and can be used to obtain images in conjunction with source 804. By shortening support arm 854 and allowing a free-standing arrangement for detector 802, the FIG. 27 configuration allows more freedom of movement for positioning radiation source 804. This can help to allow fluoroscopic imaging in situations where conventional fluoroscopy equipment does not currently fit or where practitioner access, visibility, or movement about the patient is constrained, for example.

Figure 28:
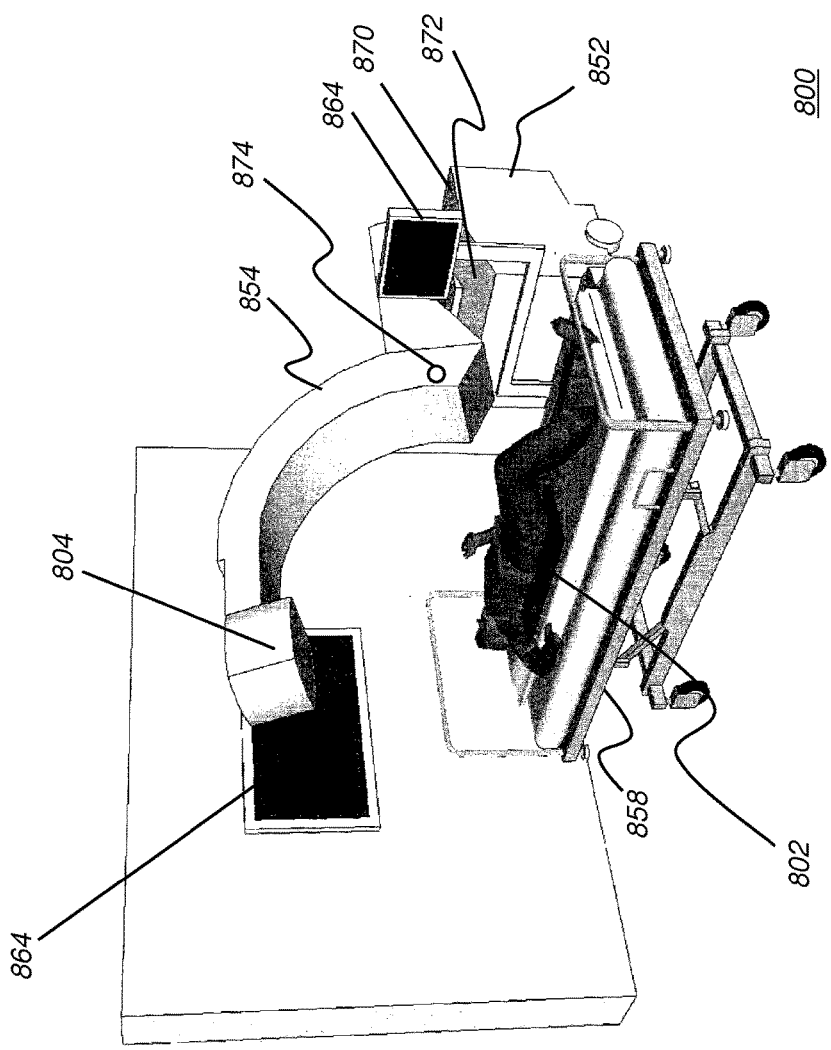
FIG. 28 shows the portable imaging apparatus with displays and processor.

As shown in FIG. 28, imaging apparatus 800 allows images to be obtained with the patient lying in a bed 858, rather than requiring the patient to be moved from bed 858 to lie on a separate platform for imaging, as shown in FIGS. 26 and 27. One or more displays 864 are coupled to a processor 870 that is housed in transport frame 852. Processor 870 provides control of the imaging sequence, as described in more detail subsequently, and obtains, processes, and displays the acquired image data from detector 802.

According to an embodiment of the application, support arm 854 is a C-arm that is movable in a number of directions relative to transport frame 852 or a stationary frame. Support arm 854 is movable in the forward and reverse directions, vertically, and laterally, or side-to-side.

Configuration of Retractable End

Figure 30:
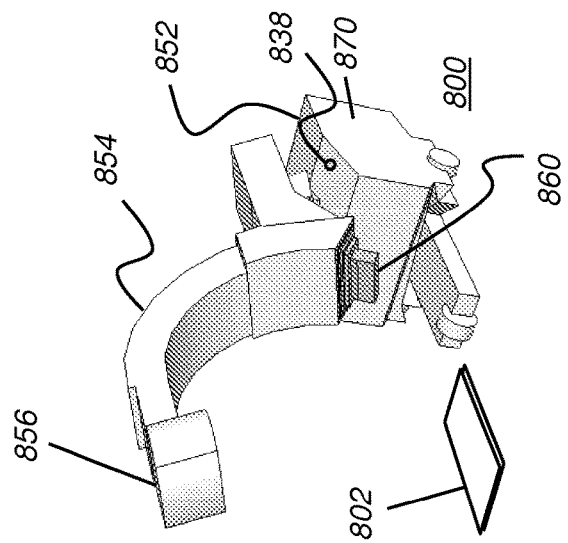
FIG. 30 shows the support arm with retractable end in the retracted position.
Figure 29:
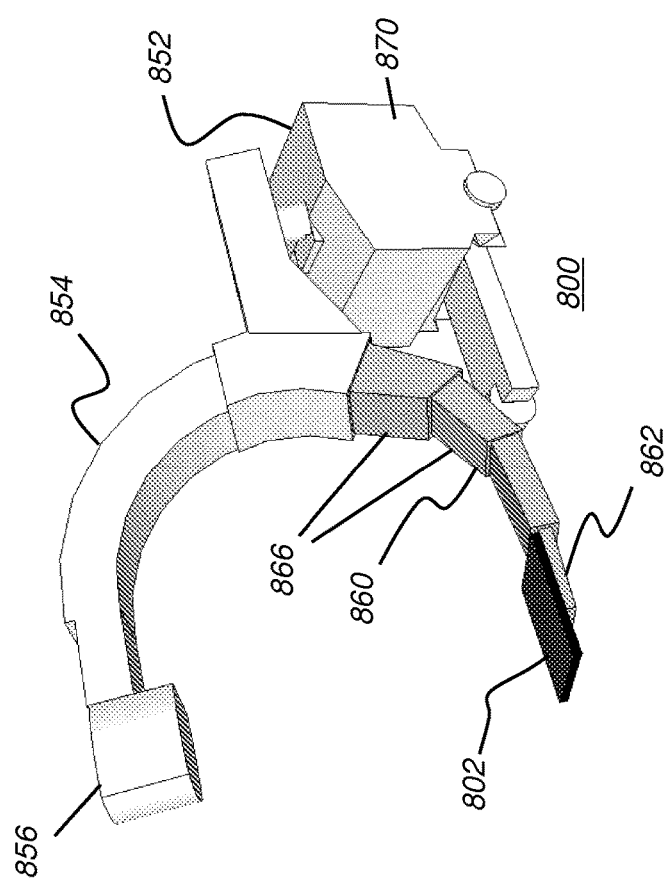
FIG. 29 shows the support arm with retractable end in the extended position.

FIG. 29 shows support arm 854 with retractable end 860 in the extended position. In certain exemplary embodiments, a retractable end of a C-arm imaging apparatus can reciprocally move between a first or extended position (e.g., imaging position) for use with a detector (e.g., embedded/built-in or detachable) and a second or retracted position (e.g., for maneuvering, storage or the like). In the embodiment shown in FIGS. 29 and 30, retractable end 860 has a number of sleeved sections 866 that extend outward or retract in a telescopic manner. FIG. 30 shows apparatus 800 with end 860 retracted. With this arrangement, imaging is performed in free-standing mode, as shown.

There are a number of mechanical and/or electro-mechanical systems and/or methods that can be used to provide retractable operation of support arm 854, known to those skilled in the mechanical arts. FIGS. 29 and 30 show a sectioned, telescopic approach for arm retraction. According to an alternate embodiment of the application, retractable end 860 is provided as a single curved piece that slides into the hollowed interior of the support arm 854. Any of a number of arrangements or motors or other actuators can be used in order to provide the needed movement for extension and retraction.

Timing and Synchronization

Certain exemplary embodiments according to the application can provide first communications between a detachable detector and an imaging apparatus (e.g., imaging apparatus controller) when mounted thereto and second communications (e.g., wireless) therebetween when the detachable detector is used for imaging but detached therefrom. In one embodiment, detector 802 can include built-in connectors so that power and communications ports are provided by imaging apparatus 800 hardware when detector 802 is seated in support 862. This can include connection to processor 870 in the portable imaging apparatus 800 for signal communication with processor 870. When the detector 802 is detached from support arm 854, detector 802 is capable of wired or wireless signal communication and interaction with processor 870. According to an alternate embodiment of the application, a detached detector imaging capability is not provided and only wired transmission is provided and a cable (not shown) connects detector 802 with power and with processor 870.

In the extended C-arm configuration of FIG. 29, detector 802 receives synchronization signals from processor 870, including signals that prepare, configure, and reset detector 802 for obtaining image data for each exposure. When in the free-standing configuration of FIG. 30, radiation source 804 is physically de-coupled from the detector 802, so that the relative positions of source 804 and detector 802 are no longer spatially fixed. Detector 802 interacts with processor 870 through either a tethered cable connection (not shown in FIG. 30) or wirelessly. The same type of synchronization timing is provided both when mounted on support 862 on the C-arm of support arm 854 and when free-standing, removed from retractable end 860.

According to an embodiment of the application, synchronization timing follows this sequence:
 (i) interaction between the processor 870 and detector 802 indicates that detector 802 is or will presently be ready for acquiring image data and that processor 870 is ready to energize the radiation source 804. This interaction typically requires transmission of signals in both directions between detector 802 and processor 870;
 (ii) a signal from, or directed through, processor 870 indicates the beginning and end of exposure;
 (iii) image data from detector 802 is acquired by processor 870; this may be provided automatically upon acquisition and initial processing of the data or in response to a prompting signal from processor 870.

The cycle of processes (i)-(iii) then can repeat as many times as needed. For a fluoroscopy system, for example, this cycle can be executed a number of times per second, with the image data results updated at a rapid rate and displayed (or stored or transmitted remotely).

Operator controls, such as controls available on display 864 for example, or controls 874 on support arm 854 or on suitable parts of apparatus 800, enable manipulation of the retractable end 860 so that it can be extended outward (e.g., partially or fully) for C-arm imaging or retracted for free-standing imaging, as needed. Referring to FIG. 28, operator controls can be available on a control console 872 or on support arm 854 (e.g., on a retractable portion or a portion always available). According to an alternate embodiment of the application, operator removal of detector 802 from support 862 can be detected and, in response, retractable end 860 can be automatically retracted into support arm 854. One or more visual indicators 838 can be provided in order to more clearly indicate that imaging apparatus 800 is in free-standing mode.

Figure 31:
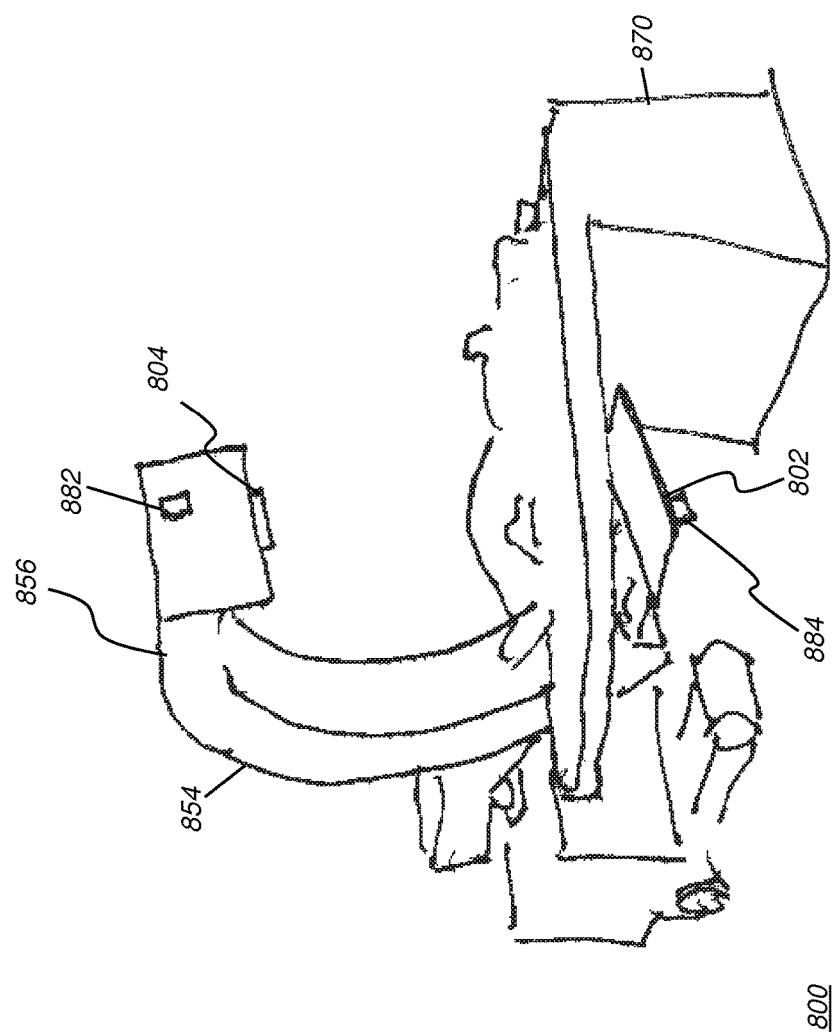
FIG. 31 is a perspective view of the imaging apparatus showing temperature sensors according to an embodiment of the present invention.

Temperature monitoring for the x-ray source and detector can be particularly useful where imaging apparatus 800 acquires images in a repeated fashion, such as for fluoroscopy, for example. FIG. 31 shows imaging apparatus 800 having a radiation source temperature sensor element 882 that provides a signal that is indicative of temperature near the x-ray tube or other radiation source and a detector temperature sensor element 884 that provides a signal indicative of detector 802 temperature. In one embodiment, a current temperature at a known spatial position relative to the source and/or detector can correspond to the actual current temperature of the source and/or the detector, respectively. Both temperature sensors 882 and 884 are in signal communication with processor 870 for reporting temperature conditions.

According to an embodiment of the application, processor 870 temporarily can stop imaging operations when either the source or detector temperature exceeds given threshold values.

Figure 32:
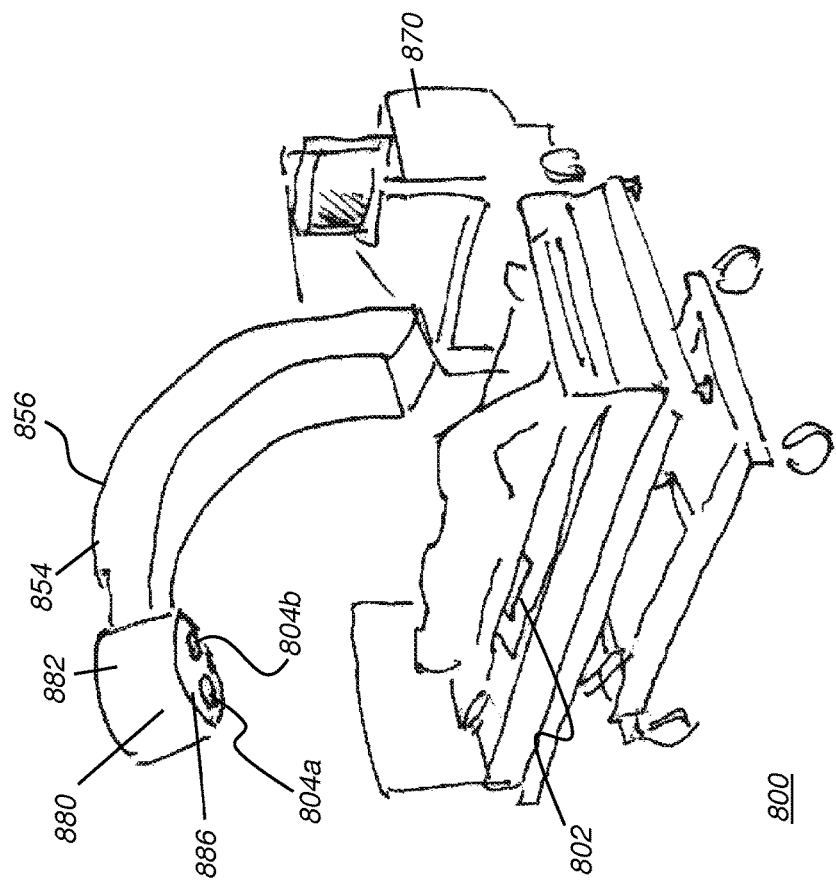
FIG. 32 is a perspective view of the imaging apparatus showing a turret for switching between two radiation sources.

Certain exemplary system and/or method embodiments according to the application can provide an imaging apparatus that can use multiple, interchangeable radiographic sources. FIG. 32 shows an alternate embodiment of imaging apparatus 800 wherein multiple radiation sources are used. As shown in FIG. 32, detector 802 is in free-standing mode. Two radiation sources 804a and 804b are shown; however, more than two sources can be used. The two or more radiation sources 804a, 804b, and so on are closely matched for beam characteristics such as focal length, for example. According to an alternate embodiment of the application, components of the x-ray generation system are shared between sources 804a and 804b. Separate calibration can be provided for each source (e.g., interchangeable source) that is used.

An actuator 880 is energizable to switch between sources 804a and 804b in response to heat sensing. In a turret 886 arrangement, actuator 880 rotates the desired source 804a or 804b into position, wherein the axis of rotation extends in the direction of the radiation beam. According to an alternate embodiment of the application, switching actuator 880 is a motor or solenoid that is operatively coupled to a reflective element or other type of guide that redirects the x-ray beam. The reflective element can be switchable so that it lies in the path of either source 804a or 804b as needed, under control of processor 870.

According to an alternate embodiment of the application, manual switching of the source is also provided for pivoting the appropriate source 804a or 804b into position. An interlocking rotating pivot could be provided for automatic or manual switching.

Figure 33:
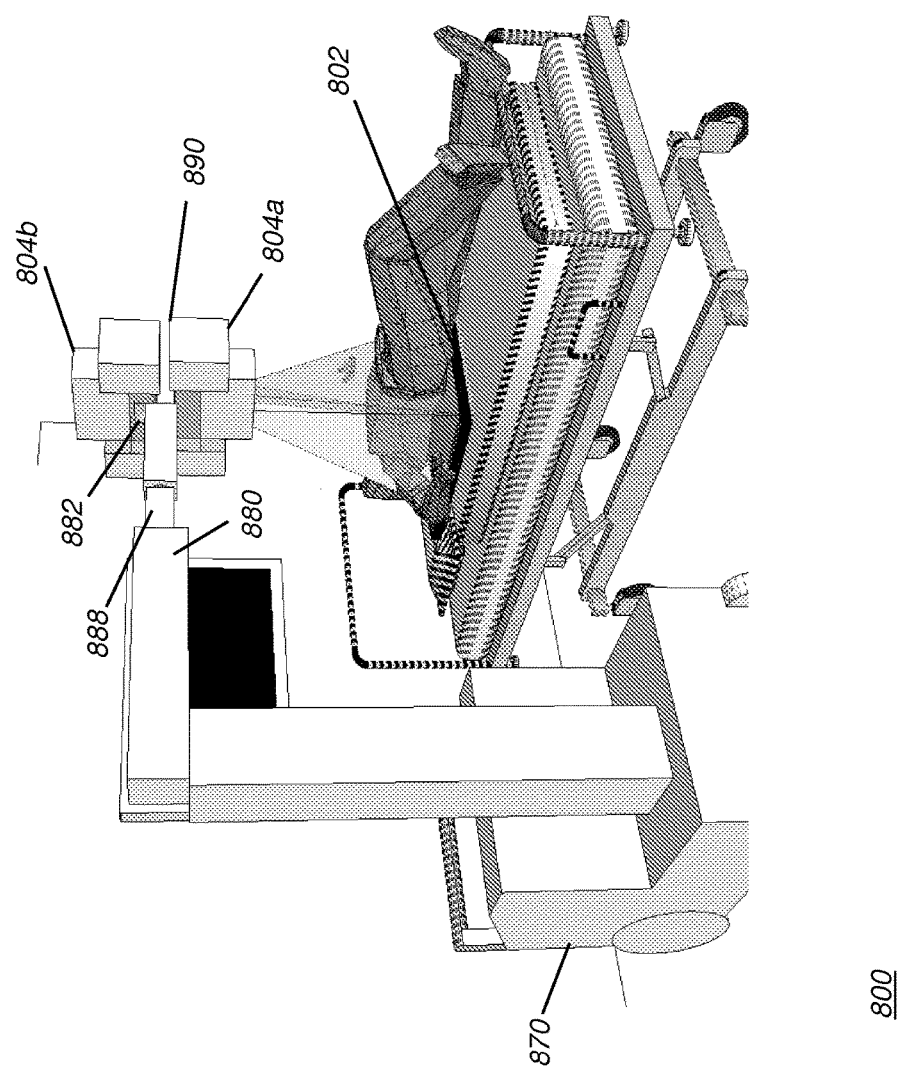
FIG. 33 shows an alternate embodiment of the present invention in which a switchable head is provided.
Figure 34:
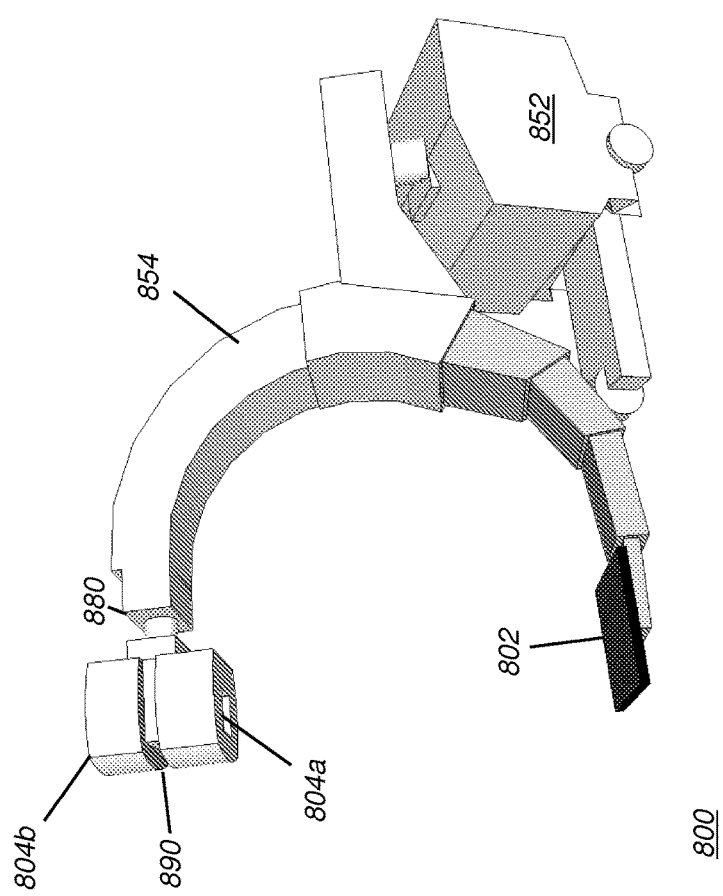
FIG. 34 shows another alternate embodiment of the present invention in which a switchable head is provided.

FIGS. 33 and 34 show alternate embodiments of the application in which a switchable head 890 is provided. Switchable head 890 is rotated to pivot either source 804a or 804b into position as needed. The axis of rotation for switching between source 804a and 804b is generally orthogonal to the direction of the radiation beam. FIG. 33 shows a system having an extendable arm 888 and a free-standing detector 802. FIG. 34 shows a system with switchable head 890 in which support arm 854 is a retractable C-arm.

According to another alternate embodiment of the application, radiation sources 804a and 804b are detachable, allowing removal and replacement.

Image Acquisition Management System

Figure 35:
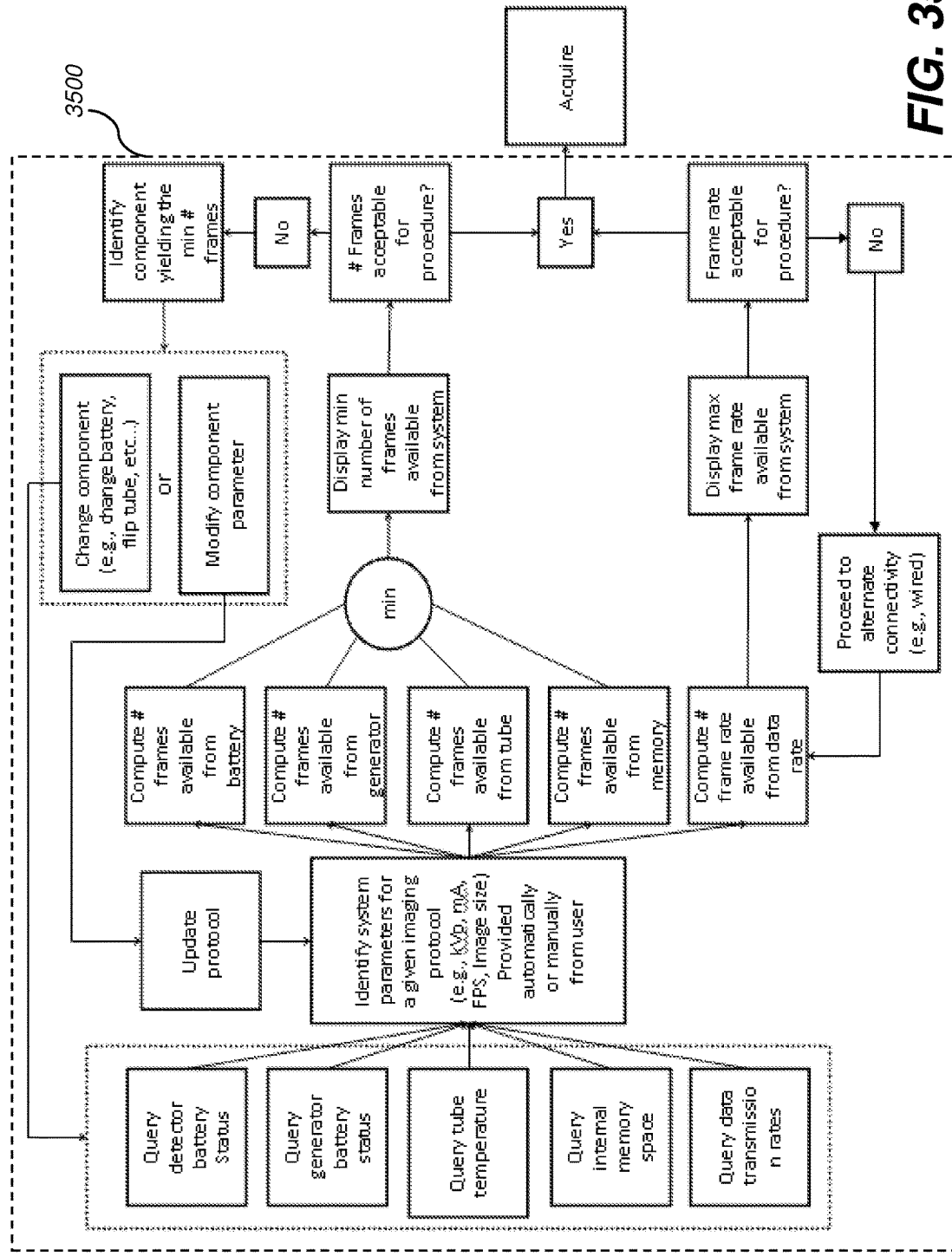
FIG. 35 is a diagram that shows exemplary operations implemented in whole or in part by exemplary image acquisition management controller system and/or method embodiments according to the application.

Certain exemplary embodiments according to the application can provide image acquisition management for a fluoroscopic imaging system including a capability to plan one or more fluoroscopic examinations and increase a likelihood such examinations can be completed. Certain exemplary embodiments according to the application can provide image acquisition management for a fluoroscopic imaging system including at least heat-capacity (e.g., temperature) limited capabilities of a radiation source, bandwidth limited communications with a wireless (e.g., detachable) detector, storage limited capability of a wireless (e.g., detachable) detector, and power (e.g., battery) limited capabilities of a wireless (e.g., detachable) detector and/or storage energy (e.g., battery) limited capabilities of a portable fluoroscopic imaging system. Thus, in one exemplary embodiment, an image acquisition management controller for a fluoroscopic imaging system, can consider or address inputs including (i) fluoroscopic procedures to be performed, (ii) expected or actual bandwidth of communications with a detector, (iii) storage capabilities of a detector (e.g., before image(s) are confirmed to be transmitted to a fluoroscopic imaging system, (iv) remaining storage energy of the wireless detector, (v) remaining heat capacity of a radiation source, and/or (vi) remaining storage energy of said fluoroscopic imaging system. FIG. 35 is a diagram that shows exemplary operations implemented in whole or in part by exemplary image acquisition management controller system and/or method embodiments according to the application.

According to such exemplary inputs, certain exemplary image acquisition management controller embodiments can modify planned or current (e.g., actual concurrent) operations of a source (e.g., reduced exposure rate, reduced exposure area, reduced exposure power) to address, control or reduce temperature and/or control or increase operational life relative to one or more fluoroscopic procedures. Further, according to such inputs, certain exemplary image acquisition management controller embodiments can modify planned or current (e.g., actual concurrent) operations of a detector to lower frame-rates and/or resolution (binning) when detector battery power is low to control or increase operational life relative to one or more fluoroscopic procedures. In addition, according to such inputs, certain exemplary image acquisition management controller embodiments can modify planned or current (e.g., actual concurrent) operations of a detector to lower frame-rates and/or resolution (binning) when bandwidth is low to implement one or more fluoroscopic procedures.

In one embodiment, an image acquisition management controller for a fluoroscopic imaging system can be implemented in processor 870. In one embodiment, an image acquisition management controller for a fluoroscopic imaging system can be monitor an interventional fluoroscopic procedure having an unknown length by providing a display to an operator of a current time until the source (e.g., source 804a) or the detector 802 needs to be changed based on current source temperature and operating mode, and current battery consumption rate and operating mode, respectively. In one embodiment, a warning can be provided to plan to interchange a source (e.g., detector) or change source operations such as exposure rate (e.g., detector operations such as lower frame-rates or data transmission rates). For example, an exposure rate of the source can be decreased or slowed to extend the source lifetime to finish the interventional operation. Upon operator action, the displayed status of the source and/or detector can be updated accordingly. In one embodiment, a display can include at least time until source overheat/replacement and/or time until detector bandwidth overflow or battery replacement. In one embodiment, a detector stores all data received during an examination until confirmation is received that transmitted portions thereof have been received and acknowledged by the imaging system. Such data storage operations can be monitored as well.

In one embodiment, an image acquisition management controller for a fluoroscopic imaging system can provide planning for a plurality of planned fluoroscopic procedures. For example, an operator may have 5 examinations with corresponding image acquisition requirements to be performed in an afternoon or set time period. Accordingly, the image acquisition management controller can provide a planned source control schedule and detector operation control or power consumption control to allow a likely completion of all 5 examinations without source or detector replacement. To complicate such analysis, additional factors can be monitored by the image acquisition management controller such as a number and condition of replacement detectors, interchangeable sources, replaceable detector batteries carried by a fluoroscopic imaging system. Further, selected fluoroscopic examination location can provide a capability to charge a portable fluoroscopic imaging system battery and/or a detector battery.

In one embodiment, an image acquisition management controller for a fluoroscopic imaging system can monitor a fluoroscopic procedure (e.g., having a known or planned procedural length/data acquisition amount) to limit or control the capabilities of the imaging system based on the wireless bandwidth available, e.g. limit to lower frame-rates and/or resolution (binning) when bandwidth is low. Alternatively, an image acquisition management controller can monitor a fluoroscopic procedure (e.g., having a known or planned procedural length/data acquisition amount) to limit or control the capabilities of the imaging to the battery power of the wireless detector, e.g. limit to lower frame-rates and/or resolution (binning) when detector battery power is low. Further, an image acquisition management controller can monitor a fluoroscopic procedure to limit or control the capabilities of the source and/or detector based on a current image quality whereby image quality can be improved as desired by improving data transmission (e.g., increase frames per second (fps), reduce binning, or the like).

FIG. 35 is a diagram that shows exemplary operations implemented in whole or in part by exemplary image acquisition management controller system and/or method embodiments according to the application. In one embodiment shown in FIG. 35, an image acquisition management controller 3500 can implement in whole or in part, various exemplary operations sufficient to plan, modify or execute a fluoroscopic procedure while addressing or insuring that adequate system resources (e.g., number of frames and/or frame rate acceptable for procedure) are available.

Certain exemplary system and/or method embodiments according to the application can provide a C-arm radiographic imaging apparatus that can use multiple, interchangeable radiographic sources. In one embodiment, multiple x-ray sources 804a and 804b (e.g., switchable head 890) can be replaced or switched responsive to a current temperature (e.g., detected by temperature sensor element 882) in order to provide more continuous or near-continuous fluoroscopic imaging. In one embodiment, before (or when) source 804a overheats to the extent that source 804a can not be used for imaging, source 804a is replaced by source 804b to increase an operational time that the apparatus (e.g., shown in FIG. 23, FIGS. 29-30 or FIG. 34) can be used. In one embodiment, the source to be switched in (e.g., source 804b) is provided with an initialization procedure or time interval to more closely match its operational characteristics to the source (e.g., source 804a) being switched out. In one embodiment, the operator (e.g., using a display GUI or the like) or the processor 870 can control the temperature monitoring and/or source (e.g., source 890, source 804a, 804b) interchange.

Consistent with at least one embodiment, exemplary methods can use a computer program with stored instructions that perform on image data that is accessed from an electronic memory. As can be appreciated by those skilled in the image processing arts, a computer program of an embodiment of the present invention can be utilized by a suitable, general-purpose computer system, such as a personal computer or workstation. However, many other types of computer systems can be used to execute the computer program of the present invention, including an arrangement of networked processors, for example. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing one method of the application may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that computer program products of this application may make use of various image manipulation algorithms and processes that are well known. It will be further understood that exemplary computer program product embodiments herein may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or cooperating with the computer program product of the present invention, are not specifically shown or described herein and may be selected from such algorithms, systems, hardware, components and elements known in the art.

Priority is claimed from commonly assigned, copending U.S. provisional patent application Ser. No. 61/708,846, filed Oct. 2, 2012, entitled "RAPID FRAME-RATE WIRELESS IMAGING SYSTEM", in the name of William J. Sehnert et al., the disclosure of which is incorporated by reference.

In addition, while a particular feature of an embodiment has been disclosed with respect to only one of several implementations or embodiments, such feature can be combined with one or more other features of the other implementations and/or other exemplary embodiments as can be desired and advantageous for any given or particular function. To the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items can be selected. Further, in the discussion and claims herein, the term "exemplary" indicates the description is used as an example, rather than implying that it is an ideal.

The invention has been described in detail with particular reference to a presently preferred embodiment, but it will be understood that variations and modifications can be effected within the spirit and scope of the invention. For example, the rib contrast suppression techniques that are used can be selected from any of a number of types of rib contrast suppression algorithm that is described in the literature. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A portable radiographic imaging apparatus for fluoroscopy comprising:
   a wheeled transport frame;
   a C-shaped support arm mounted on the frame;
   radiation sources attached to a fixed end of the support arm;
   a radiation detector attached to a retractable end of the support arm when the retractable end is extended outward from the support arm, the retractable end opposite the fixed end, wherein the radiation sources comprise two or more radiation sources that are individually energizable to emit a radiation beam toward the retractable end, the imaging detector is removable from the retractable end for free-standing operation, and wherein the retractable end is configured to retract into an interior space of the support arm;
   a rotatable switching actuator that is configured to replace one of the radiation sources by simultaneously rotating into position a new radiation source while rotating out of position said replaced one of the radiation sources and to align the radiation beams from each of the new and replaced radiation sources along the same optical path;
   a temperature sensor that provides a signal indicative of a temperature near an energized radiation source; and
   a processor configured to monitor the signal from the temperature sensor, and to control energization of the two or more radiation sources according to the monitored signal.

2. The portable radiographic imaging apparatus for fluoroscopy according to claim 1, further comprising a collimator, wherein the processor is configured to detect an orientation of the radiation detector relative to one of the radiation sources and to adjust an aperture of the collimator to shape the radiation beam for incidence on a predetermined area of the radiation detector.

3. The portable radiographic imaging apparatus of claim 1, further comprising a collimator having an aperture to shape an x-ray beam emitted by the radiation sources, the collimator including a plurality of collimator blades to define a non-rectangular shape of the aperture.

4. The portable radiographic imaging apparatus of claim 1, wherein the radiation detector is configured to capture radiographic images at a rate greater than one image per second.

5. The portable radiographic imaging apparatus of claim 1, wherein the processor is further configured to wirelessly communicate with the radiation detector, and wherein the radiation detector comprises a wireless transmitter to transmit radiographic images to the processor.

6. The portable radiographic imaging apparatus of claim 1, wherein the retractable end comprises jointed sections that telescope inward and outward, and wherein the detector and radiation source cooperate to expose and acquire radiographic image data according to a synchronization signal.

7. The portable radiographic imaging apparatus of claim 1, wherein the retractable end is configured to retract automatically when the radiation detector is removed therefrom.

8. A portable radiographic imaging apparatus comprising:
   a transport frame having wheels to rollably transport the portable radiographic imaging apparatus;
   a C-shaped support arm mounted on the transport frame;
   radiation sources attached to a fixed end of the support arm;
   a radiation detector attached to a retractable end of the support arm, the retractable end of the support arm opposite the fixed end of the support arm; and
   a rotatable actuator attached to the fixed end of the support arm, the rotatable actuator configured to replace one of the radiation sources by simultaneously rotating into an imaging position a new radiation source while rotating out of the imaging position the replaced one of the radiation sources, and to align the radiation beams emitted from each of the new and replaced radiation sources along the same optical path when in the imaging position.

9. The portable radiographic imaging apparatus of claim 8, wherein the radiation sources comprise two or more radiation sources that are individually energizable to emit a radiation beam toward the retractable end.

10. The portable radiographic imaging apparatus of claim 8, wherein the imaging detector is removable from the retractable end for free-standing operation.

11. The portable radiographic imaging apparatus of claim 10, wherein the retractable end is configured to retract into an interior space of the support arm.

12. The portable radiographic imaging apparatus of claim 8, further comprising a temperature sensor configured to provide a signal indicative of a temperature near an energized radiation source.

13. The portable radiographic imaging apparatus of claim 12, further comprising a processor configured to monitor the signal from the temperature sensor, and to control activation of the radiation sources in response to the monitored signal.

14. The portable radiographic imaging apparatus of claim 8, further comprising a collimator having an adjustable aperture to shape the radiation beams emitted from the radiation sources for incidence on a predetermined area of the radiation detector.

15. The portable radiographic imaging apparatus of claim 14, wherein the collimator comprises individual collimator blades configured to define a non-rectangular shape of the adjustable aperture.

16. The portable radiographic imaging apparatus of claim 8, wherein the radiation detector is configured to capture radiographic images at a rate greater than one image per second.

17. The portable radiographic imaging apparatus of claim 16, wherein the radiation detector comprises a wireless transmitter to transmit the captured radiographic images wirelessly during free-standing operation.

18. The portable radiographic imaging apparatus of claim 8, wherein the retractable end of the support arm comprises telescoping extendable and retractable sections that extend inward and outward.

19. A method of operating a portable radiographic imaging apparatus, the method comprising:

attaching an adjustable support arm to the portable radiographic imaging apparatus;

attaching radiation sources to a first end of the support arm;

transporting the portable radiographic imaging apparatus to a position adjacent a patient in a bed using wheels attached to the portable radiographic imaging apparatus;

positioning a radiation detector on one side of the patient;

adjusting an imaging position of a first one of the radiation sources to align a central axis of a radiation beam emitted by the first one of the radiation sources toward the detector; and simultaneously rotating into the imaging position a second one of the radiation sources while rotating out of the imaging position the first one of the radiation sources, and aligning a central axis of a radiation beam emitted by the second one of the radiation sources with the central axis of the radiation beam emitted by the first one of the radiation sources, wherein the first and second radiation sources are rotated about a common axis.

20. The method of claim 19, further comprising attaching the radiation detector to a second end of the support arm opposite the first end of the support arm before the step of positioning the radiation detector.

* * * * *